(12) United States Patent
Parihar et al.

(10) Patent No.: US 8,702,623 B2
(45) Date of Patent: Apr. 22, 2014

(54) BIOPSY DEVICE WITH DISCRETE TISSUE CHAMBERS

(75) Inventors: Shailendra K. Parihar, Mason, OH (US); John A. Hibner, Mason, OH (US); Michael R. Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 808 days.

(21) Appl. No.: 12/337,911

(22) Filed: Dec. 18, 2008

(65) Prior Publication Data

US 2010/0160824 A1    Jun. 24, 2010

(51) Int. Cl.
*A61B 10/00* (2006.01)

(52) U.S. Cl.
USPC ........... 600/568; 600/566; 600/567; 606/169; 606/170; 606/171

(58) Field of Classification Search
USPC .................. 600/562–572; 606/167, 170, 180
See application file for complete search history.

(56) References Cited

U.S. PATENT DOCUMENTS

| | | | |
|---|---|---|---|
| 2,853,071 A | 9/1958 | Saffir | |
| 3,630,192 A | 12/1971 | Jamshidi | |
| 3,719,086 A | 3/1973 | Bannister et al. | |
| 3,732,858 A | 5/1973 | Banko | |
| 3,734,099 A | 5/1973 | Bender et al. | |
| 3,889,657 A | 6/1975 | Baumgarten | |
| 3,897,216 A * | 7/1975 | Jones ............................ | 422/561 |
| 3,945,375 A | 3/1976 | Banko | |
| 3,994,297 A | 11/1976 | Kopf | |
| 3,996,935 A | 12/1976 | Banko | |
| 4,051,852 A | 10/1977 | Villari | |
| 4,083,706 A | 4/1978 | Wiley | |
| 4,203,444 A | 5/1980 | Bonnell et al. | |
| 4,257,425 A | 3/1981 | Ryan | |
| 4,316,465 A | 2/1982 | Dotson, Jr. | |
| 4,320,761 A | 3/1982 | Haddad | |
| 4,368,734 A | 1/1983 | Banko | |
| 4,393,879 A | 7/1983 | Milgrom | |

(Continued)

FOREIGN PATENT DOCUMENTS

| | | |
|---|---|---|
| EP | 378692 | 7/1990 |
| EP | 0890339 | 1/1999 |

(Continued)

OTHER PUBLICATIONS

U.S. Appl. No. 12/337,674, filed Dec. 18, 2008, Parihar et al.

(Continued)

*Primary Examiner* — Rene Towa
(74) *Attorney, Agent, or Firm* — Frost Brown Todd LLC

(57) ABSTRACT

A biopsy device includes a probe, a holster, and a tissue sample holder for collecting tissue samples. The probe includes a needle and a hollow cutter. The tissue sample holder includes a housing having a plurality of chambers that are respectively configured to receive a tray. The housing is releasably engageable with the probe. Each tray is configured to receive a tissue sample communicated through the cutter lumen. Each tray is removable from the housing, such as along an axial direction. The tissue sample holder is rotatable to successively index each chamber to the cutter lumen. A tray retainer is operable to selectively secure the trays relative to the housing. The trays may be flexible, resilient, or rigid.

18 Claims, 17 Drawing Sheets

(56) References Cited

U.S. PATENT DOCUMENTS

| | | |
|---|---|---|
| 4,517,977 A | 5/1985 | Frost |
| 4,554,473 A | 11/1985 | Muller |
| 4,600,014 A | 7/1986 | Beraha |
| 4,782,833 A | 11/1988 | Einhorn et al. |
| 4,919,146 A | 4/1990 | Rhinehart et al. |
| RE33,258 E | 7/1990 | Onik et al. |
| 4,989,614 A | 2/1991 | Dejter, Jr. et al. |
| 4,995,877 A | 2/1991 | Ams et al. |
| 5,047,008 A | 9/1991 | de Juan, Jr. et al. |
| 5,108,381 A | 4/1992 | Kolozsi |
| 5,112,299 A | 5/1992 | Pascaloff |
| 5,120,003 A * | 6/1992 | Sacconi ........................ 242/317 |
| 5,133,359 A | 7/1992 | Kedem |
| 5,197,484 A | 3/1993 | Kornberg et al. |
| 5,213,110 A | 5/1993 | Kedem et al. |
| 5,217,478 A | 6/1993 | Rexroth |
| 5,217,479 A | 6/1993 | Shuler |
| 5,226,909 A | 7/1993 | Evans et al. |
| 5,231,110 A | 7/1993 | Seele et al. |
| 5,234,000 A | 8/1993 | Hakky et al. |
| 5,249,121 A | 9/1993 | Baum et al. |
| 5,275,609 A | 1/1994 | Pingleton et al. |
| 5,290,303 A | 3/1994 | Pingleton et al. |
| 5,295,980 A | 3/1994 | Ersek |
| 5,312,425 A | 5/1994 | Evans et al. |
| 5,320,110 A | 6/1994 | Wang |
| 5,320,635 A | 6/1994 | Smith |
| 5,341,816 A | 8/1994 | Allen |
| 5,353,804 A | 10/1994 | Kornberg et al. |
| 5,403,276 A | 4/1995 | Schechter et al. |
| 5,406,959 A | 4/1995 | Mann |
| 5,415,169 A | 5/1995 | Siczek et al. |
| 5,423,844 A | 6/1995 | Miller |
| 5,424,625 A | 6/1995 | Haner |
| 5,431,645 A | 7/1995 | Smith et al. |
| 5,432,065 A | 7/1995 | Fuller |
| 5,439,457 A | 8/1995 | Yoon |
| 5,455,766 A | 10/1995 | Scheller et al. |
| 5,505,210 A | 4/1996 | Clement |
| 5,520,635 A | 5/1996 | Gelbfish |
| 5,526,822 A | 6/1996 | Burbank et al. |
| 5,532,168 A | 7/1996 | Marantz |
| 5,543,695 A | 8/1996 | Culp et al. |
| 5,580,347 A | 12/1996 | Reimels |
| 5,601,585 A | 2/1997 | Banik et al. |
| 5,624,418 A * | 4/1997 | Shepard ........................ 604/319 |
| 5,643,304 A | 7/1997 | Schechter et al. |
| 5,645,209 A | 7/1997 | Green et al. |
| 5,649,547 A | 7/1997 | Ritchart et al. |
| 5,669,923 A | 9/1997 | Gordon |
| 5,685,840 A | 11/1997 | Schechter et al. |
| 5,689,159 A | 11/1997 | Culp et al. |
| 5,769,086 A | 6/1998 | Ritchart et al. |
| 5,775,333 A | 7/1998 | Burbank et al. |
| 5,791,908 A | 8/1998 | Gillio |
| 5,804,936 A | 9/1998 | Brodsky et al. |
| 5,823,998 A | 10/1998 | Yamagata |
| 5,848,978 A | 12/1998 | Cecchi |
| 5,871,454 A | 2/1999 | Majlessi |
| 5,873,967 A | 2/1999 | Clark et al. |
| 5,876,329 A | 3/1999 | Harhen |
| 5,910,139 A | 6/1999 | Cochran et al. |
| 5,913,857 A | 6/1999 | Ritchart et al. |
| 5,928,164 A | 7/1999 | Burbank et al. |
| 5,944,673 A | 8/1999 | Gregoire et al. |
| 5,964,716 A | 10/1999 | Gregoire et al. |
| 5,976,164 A | 11/1999 | Bencini et al. |
| 5,980,469 A | 11/1999 | Burbank et al. |
| 6,007,497 A | 12/1999 | Huitema |
| 6,013,956 A | 1/2000 | Anderson, Jr. |
| 6,017,316 A | 1/2000 | Ritchart et al. |
| 6,019,733 A | 2/2000 | Farascioni |
| 6,042,593 A | 3/2000 | Storz et al. |
| 6,050,955 A | 4/2000 | Bryan et al. |
| 6,061,446 A | 5/2000 | Lester et al. |
| 6,077,230 A | 6/2000 | Gregoire et al. |
| 6,080,113 A | 6/2000 | Heneveld et al. |
| 6,083,177 A | 7/2000 | Kobren et al. |
| 6,086,544 A | 7/2000 | Hibner et al. |
| 6,096,042 A | 8/2000 | Herbert |
| 6,106,512 A | 8/2000 | Cochran et al. |
| 6,120,462 A | 9/2000 | Hibner et al. |
| 6,120,733 A | 9/2000 | Goodman et al. |
| 6,142,946 A | 11/2000 | Hwang et al. |
| 6,142,955 A | 11/2000 | Farascioni et al. |
| 6,142,956 A | 11/2000 | Kortenbach et al. |
| 6,162,187 A | 12/2000 | Buzzard et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,245,084 B1 | 6/2001 | Mark et al. |
| 6,273,862 B1 | 8/2001 | Privitera et al. |
| 6,346,107 B1 | 2/2002 | Cucin |
| 6,402,701 B1 | 6/2002 | Kaplan et al. |
| 6,409,970 B1 | 6/2002 | Phifer |
| 6,428,486 B2 | 8/2002 | Ritchart et al. |
| 6,428,487 B1 | 8/2002 | Burdorff et al. |
| 6,436,054 B1 | 8/2002 | Viola et al. |
| 6,444,174 B1 * | 9/2002 | Lascombes ................... 422/554 |
| 6,485,436 B1 | 11/2002 | Truckai et al. |
| 6,488,636 B2 | 12/2002 | Bryan et al. |
| 6,527,731 B2 | 3/2003 | Weiss et al. |
| 6,544,194 B1 | 4/2003 | Kortenbach et al. |
| 6,551,253 B2 | 4/2003 | Worm et al. |
| 6,585,664 B2 | 7/2003 | Burdorff et al. |
| 6,592,530 B1 | 7/2003 | Farhadi |
| 6,602,203 B2 | 8/2003 | Stephens et al. |
| 6,602,227 B1 | 8/2003 | Cimino et al. |
| 6,620,111 B2 | 9/2003 | Stephens et al. |
| 6,626,849 B2 | 9/2003 | Huitema et al. |
| 6,638,235 B2 | 10/2003 | Miller et al. |
| 6,656,428 B1 | 12/2003 | Clark et al. |
| 6,659,338 B1 | 12/2003 | Dittmann et al. |
| 6,712,774 B2 | 3/2004 | Voegele et al. |
| 6,749,576 B2 | 6/2004 | Bauer |
| 6,752,768 B2 | 6/2004 | Burdorff et al. |
| 6,758,824 B1 | 7/2004 | Miller et al. |
| 6,849,080 B2 | 2/2005 | Lee et al. |
| 6,904,305 B2 | 6/2005 | Tsekos |
| 6,923,809 B2 | 8/2005 | Eggers et al. |
| 6,986,748 B2 | 1/2006 | McAlister et al. |
| 6,993,375 B2 | 1/2006 | Burbank et al. |
| 6,996,433 B2 | 2/2006 | Burbank et al. |
| 6,996,443 B2 | 2/2006 | Marshall et al. |
| 7,001,341 B2 | 2/2006 | Gellman et al. |
| 7,025,098 B2 | 4/2006 | Osborne |
| 7,025,732 B2 | 4/2006 | Thompson et al. |
| 7,047,063 B2 | 5/2006 | Burbank et al. |
| 7,053,586 B2 | 5/2006 | Jones |
| 7,108,660 B2 | 9/2006 | Stephens et al. |
| 7,153,274 B2 | 12/2006 | Stephens et al. |
| 7,156,815 B2 | 1/2007 | Leigh et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart et al. |
| 7,229,439 B2 | 6/2007 | Burbank et al. |
| 7,252,641 B2 | 8/2007 | Thompson et al. |
| 7,276,032 B2 | 10/2007 | Hibner |
| 7,278,991 B2 | 10/2007 | Morris et al. |
| 7,372,510 B2 | 5/2008 | Abileah |
| 7,419,472 B2 | 9/2008 | Hibner et al. |
| 7,438,692 B2 | 10/2008 | Tsonton et al. |
| 7,442,171 B2 | 10/2008 | Stephens et al. |
| 7,445,739 B2 | 11/2008 | Tsonton et al. |
| 7,465,279 B2 | 12/2008 | Beckman et al. |
| 7,470,237 B2 | 12/2008 | Beckman et al. |
| 7,488,295 B2 | 2/2009 | Burbank et al. |
| 7,497,833 B2 | 3/2009 | Miller |
| 7,517,322 B2 | 4/2009 | Weikel, Jr. et al. |
| 7,556,622 B2 | 7/2009 | Mark et al. |
| 7,575,556 B2 | 8/2009 | Speeg et al. |
| 7,641,668 B2 | 1/2010 | Perry et al. |
| 7,645,240 B2 | 1/2010 | Thompson et al. |

(56) References Cited

U.S. PATENT DOCUMENTS

| | | |
|---|---|---|
| 7,662,109 B2 | 2/2010 | Hibner |
| 7,736,382 B2 | 6/2010 | Webb et al. |
| 7,740,594 B2 | 6/2010 | Hibner |
| 7,740,596 B2 | 6/2010 | Hibner |
| 7,740,597 B2 | 6/2010 | Cicenas et al. |
| 7,749,172 B2 | 7/2010 | Schwindt |
| 7,753,857 B2 | 7/2010 | Hibner |
| 7,758,515 B2 | 7/2010 | Hibner |
| 7,806,834 B2 | 10/2010 | Beckman et al. |
| 7,819,819 B2 | 10/2010 | Quick et al. |
| 7,828,745 B2 | 11/2010 | McAlister et al. |
| 7,828,748 B2 | 11/2010 | Hibner |
| 7,854,706 B2 | 12/2010 | Hibner |
| 7,858,038 B2 | 12/2010 | Andreyko et al. |
| 7,867,173 B2 | 1/2011 | Hibner et al. |
| 7,896,817 B2 | 3/2011 | Garrison |
| 7,914,464 B2 | 3/2011 | Burdorff et al. |
| 7,985,239 B2 | 7/2011 | Suzuki |
| 8,002,713 B2 | 8/2011 | Heske et al. |
| 8,016,772 B2 | 9/2011 | Heske et al. |
| 8,016,844 B2 | 9/2011 | Privitera et al. |
| 8,038,627 B2 | 10/2011 | Hibner |
| 8,105,849 B2 | 1/2012 | McDevitt et al. |
| 8,118,755 B2 | 2/2012 | Hibner et al. |
| 8,172,773 B2 | 5/2012 | Heske et al. |
| 8,177,728 B2 | 5/2012 | Hibner et al. |
| 8,177,729 B2 | 5/2012 | Hibner et al. |
| 8,206,316 B2 | 6/2012 | Hibner et al. |
| 8,235,913 B2 | 8/2012 | Hibner et al. |
| 8,241,226 B2 | 8/2012 | Hibner et al. |
| 8,262,586 B2 | 9/2012 | Almazon et al. |
| 8,282,573 B2 | 10/2012 | Shabaz et al. |
| 8,480,595 B2 | 7/2013 | Speeg et al. |
| 8,485,987 B2 | 7/2013 | Videbaek et al. |
| 2002/0120212 A1 | 8/2002 | Ritchart et al. |
| 2003/0125639 A1 | 7/2003 | Fisher et al. |
| 2003/0199753 A1 | 10/2003 | Hibner et al. |
| 2003/0199785 A1 | 10/2003 | Hibner et al. |
| 2005/0004559 A1 | 1/2005 | Quick et al. |
| 2005/0049521 A1 | 3/2005 | Miller et al. |
| 2005/0082518 A1 | 4/2005 | Kunitz |
| 2005/0215922 A1 | 9/2005 | Tsonton et al. |
| 2005/0256445 A1 | 11/2005 | Cucin |
| 2005/0277829 A1 | 12/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner |
| 2006/0085759 A1 | 4/2006 | Knapheide |
| 2006/0258955 A1* | 11/2006 | Hoffman et al. ............. 600/564 |
| 2006/0258956 A1 | 11/2006 | Haberstich et al. |
| 2006/0282012 A1 | 12/2006 | McAlister et al. |
| 2007/0010738 A1 | 1/2007 | Mark et al. |
| 2007/0032742 A1 | 2/2007 | Monson et al. |
| 2007/0055173 A1 | 3/2007 | DeLonzor et al. |
| 2007/0112751 A1 | 5/2007 | Pyun |
| 2007/0167736 A1 | 7/2007 | Dietz et al. |
| 2007/0191732 A1 | 8/2007 | Voegele |
| 2007/0239067 A1* | 10/2007 | Hibner et al. ............. 600/567 |
| 2007/0255170 A1 | 11/2007 | Hibner et al. |
| 2008/0004545 A1 | 1/2008 | Garrison |
| 2008/0082021 A1 | 4/2008 | Ichikawa et al. |
| 2008/0195066 A1* | 8/2008 | Speeg et al. ............. 604/326 |
| 2008/0214955 A1 | 9/2008 | Speeg et al. |
| 2008/0221479 A1 | 9/2008 | Ritchie et al. |
| 2009/0192408 A1 | 7/2009 | Mark |
| 2010/0075664 A1 | 3/2010 | Maucksch |
| 2010/0152610 A1 | 6/2010 | Parihar et al. |
| 2010/0160824 A1 | 6/2010 | Parihar et al. |

FOREIGN PATENT DOCUMENTS

| | | |
|---|---|---|
| EP | 0995400 | 4/2000 |
| EP | 1040790 | 10/2000 |
| EP | 1074271 | 2/2001 |
| EP | 1520518 | 4/2005 |
| EP | 1642533 | 4/2006 |
| EP | 1815815 | 8/2007 |
| EP | 1832234 | 9/2007 |
| EP | 1 932 482 | 6/2008 |
| EP | 1932481 | 6/2008 |
| EP | 1932482 | 6/2008 |
| GB | 2018601 | 10/1979 |
| RU | 2021770 | 10/1994 |
| WO | WO 90/08508 | 9/1990 |
| WO | WO 93/14707 | 8/1993 |
| WO | WO 95/25465 | 9/1995 |
| WO | WO 97/24991 | 7/1997 |
| WO | WO 98/06338 | 2/1998 |
| WO | WO 98/25556 | 6/1998 |
| WO | WO 03/077768 | 9/2003 |
| WO | WO 2004/016177 | 2/2004 |
| WO | WO 2004/052179 | 6/2004 |
| WO | WO 2004/052212 | 6/2004 |
| WO | WO 2004/075728 | 9/2004 |
| WO | WO 2006/005342 | 1/2006 |
| WO | WO 2006/124489 | 11/2006 |
| WO | WO 2007/019152 | 2/2007 |
| WO | WO 2007/019445 | 2/2007 |
| WO | WO 2007/021904 | 2/2007 |
| WO | WO 2007/112751 | 10/2007 |
| WO | WO 2008/076712 | 6/2008 |

OTHER PUBLICATIONS

U.S. Appl. No. 12/337,814, filed Dec. 18, 2008, Parihar et al.
U.S. Appl. No. 12/337,872, filed Dec. 18, 2008, Parihar et al.
U.S. Appl. No. 12/337,874, filed Dec. 18, 2008, Parihar et al.
U.S. Appl. No. 12/337,942, filed Dec. 18, 2008, Parihar et al.
U.S. Appl. No. 60/869,736, filed Dec. 13, 2006, Ritchie et al.
U.S. Appl. No. 60/874,792, filed Dec. 13, 2006, Hibner et al.
International Preliminary Report on Patentability dated Jun. 21, 2011 for Application No. PCT/US2009/067165.
International Search Report dated Mar. 16, 2010 for Application No. PCT/US2009/067165.

* cited by examiner

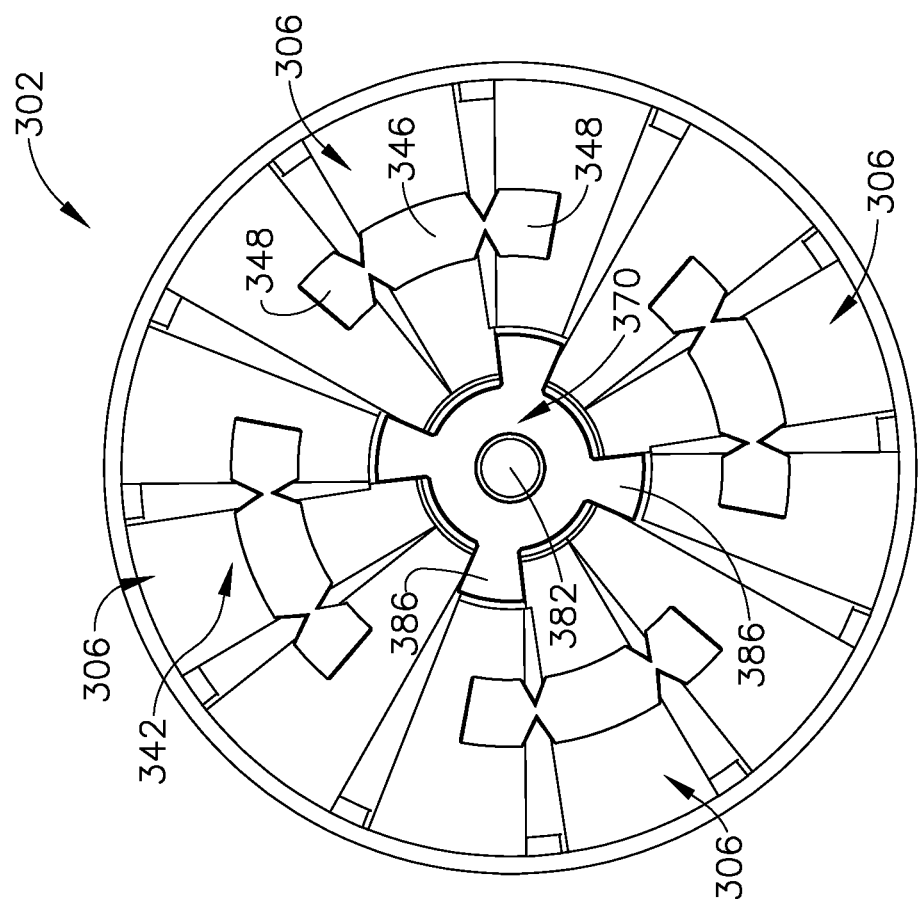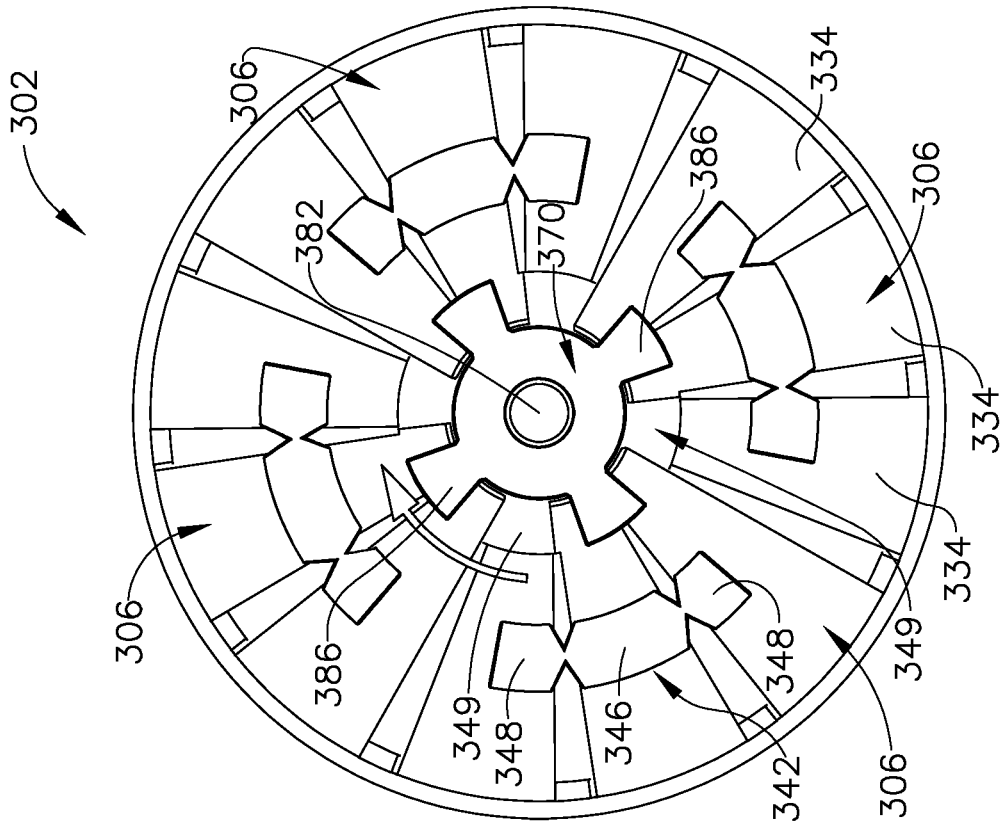
FIG. 10B
FIG. 10A

BIOPSY DEVICE WITH DISCRETE TISSUE CHAMBERS

BACKGROUND

Biopsy samples have been obtained in a variety of ways in various medical procedures using a variety of devices. Biopsy devices may be used under stereotactic guidance, ultrasound guidance, MRI (magnetic resonance imaging) guidance, PEM (positron emission mammography) guidance, BSGI (breast-specific gamma imaging) guidance, MBI (molecular breast imaging) guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 8, 2008; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. Patents, U.S. Patent Application Publications, and U.S. Provisional Patent Applications is incorporated by reference herein. While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIGS. 10A and 10B are partial end views of the tissue sample holder of FIG. 6, showing a series where a tissue tray lock is rotated to permit removal of tissue trays from the tissue sample holder;

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
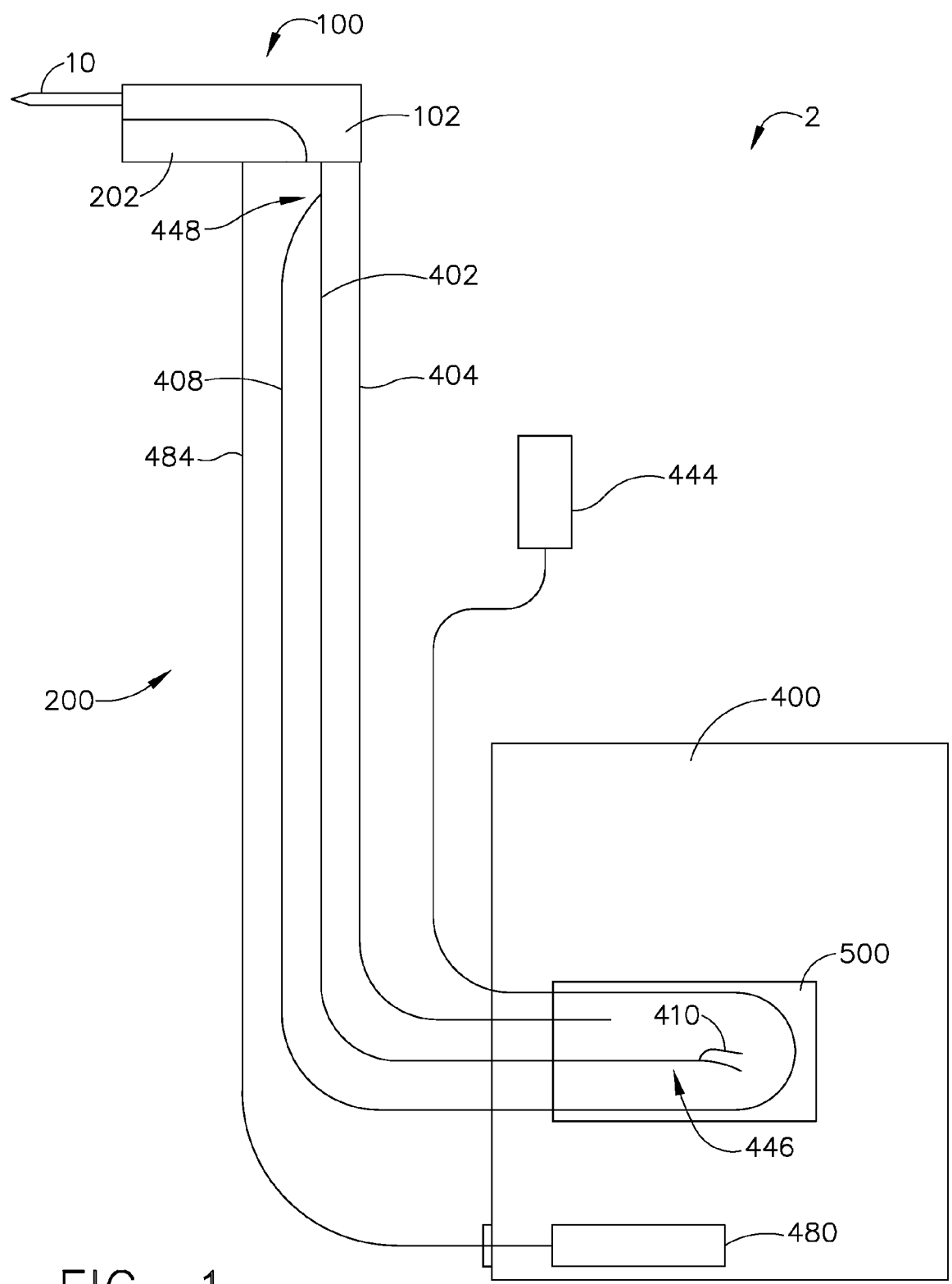
FIG. 1 is a schematic view of an exemplary biopsy system.
Figure 2:
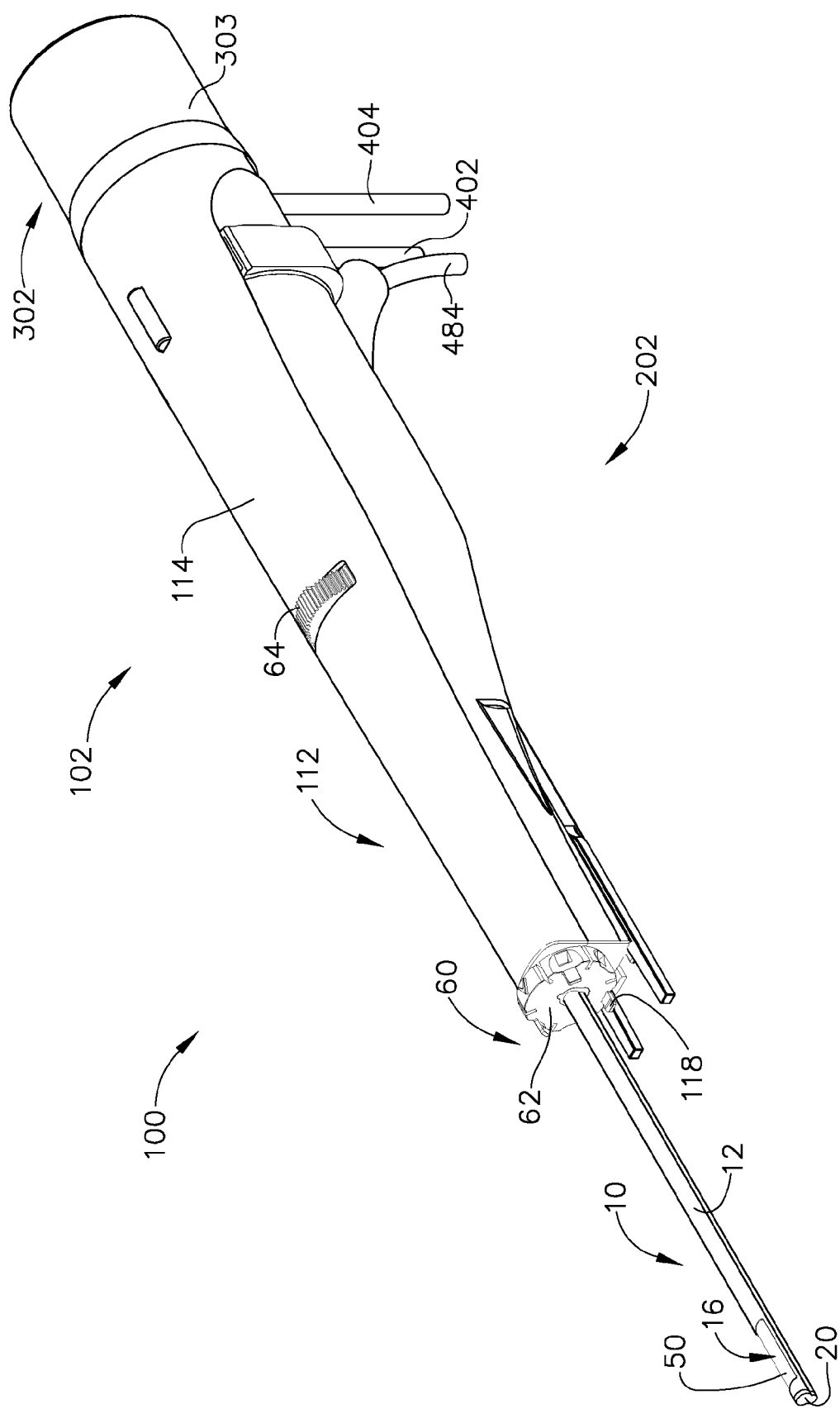
FIG. 2 is a perspective view of an exemplary biopsy device.
Figure 3:
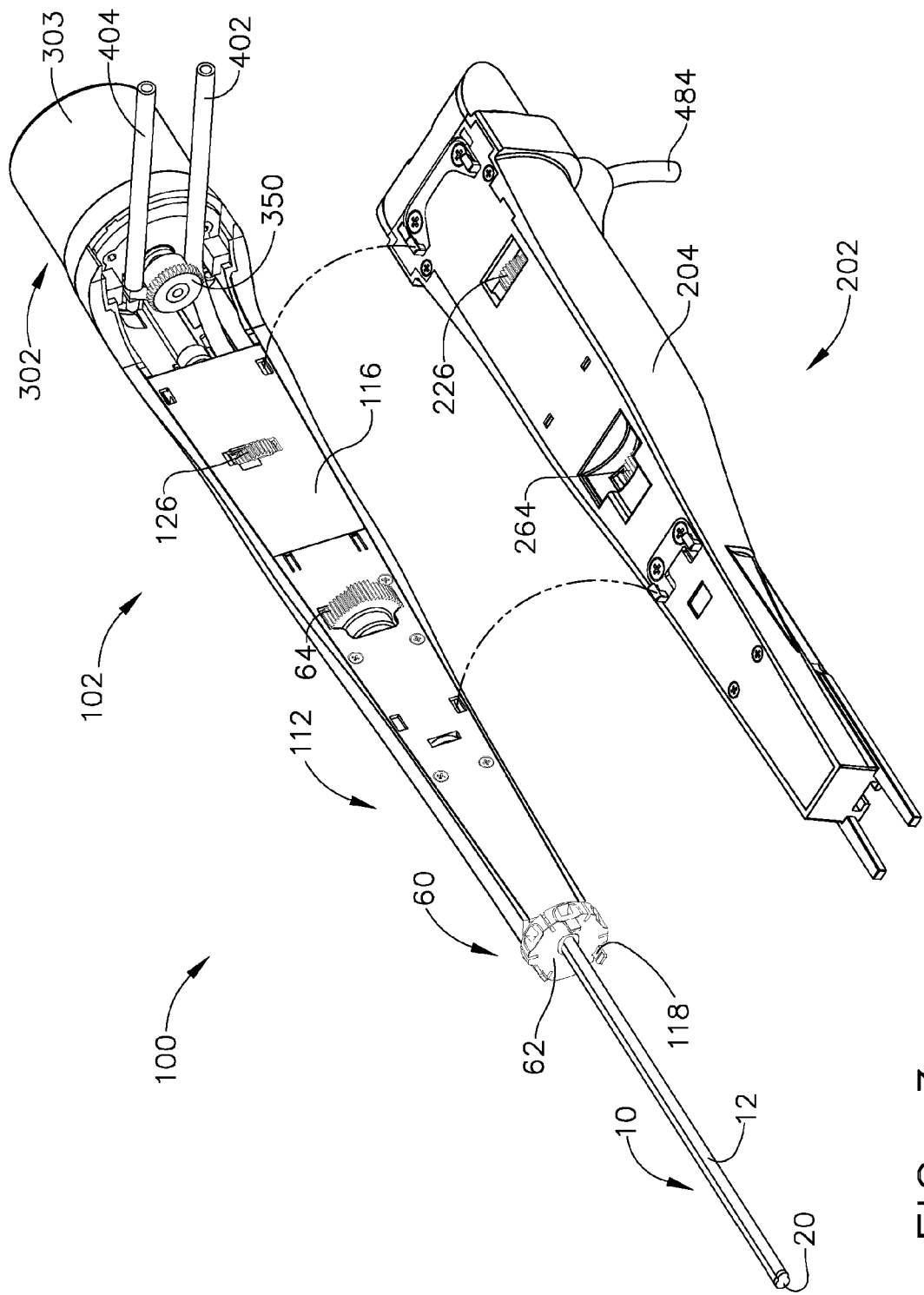
FIG. 3 is a perspective view of the biopsy device of FIG. 2, showing the probe portion decoupled from the holster portion.

As shown in FIG. 1, an exemplary biopsy system (2) includes a biopsy device (100) and a vacuum control module (400). As shown in FIGS. 2-3, biopsy device (100) comprises a probe (102), a holster (202), and a tissue sample holder (302). As will be described in greater detail below and as shown in FIG. 3, probe (102) is separable from its corresponding holster (202). Use of the term "holster" herein should not be read as requiring any portion of probe (102) to be inserted into any portion of holster (202). Indeed, in some variations of biopsy devices (100), probe (102) may simply sit on holster (202). In some other variations, a portion of holster (202) may be inserted into probe (102). Furthermore, in some biopsy devices (100), probe (102) and holster (202) may be of unitary or integral construction, such that the two components cannot be separated. Still other suitable structural and functional relationships between probe (102) and holster (202) will be apparent to those of ordinary skill in the art in view of the teachings herein.

Some variations of biopsy devices (100) may include one or more sensors (not shown), in probe (102) and/or in holster (202), that is/are configured to detect when probe (102) is coupled with holster (202). Such sensors or other features may further be configured to permit only certain types of probes (102) and holsters (202) to be coupled together. In addition or in the alternative, such sensors may be configured to disable one or more functions of probes (102) and/or holsters (202) until a suitable probe (102) and holster (202) are coupled together. Of course, such sensors and features may be varied or omitted as desired.

By way of example only, probe (102) may be provided as a disposable component, while holster (202) may be provided as a reusable component. Vacuum control module (400) is provided on a cart (not shown) in the present example, though like other components described herein, a cart is merely optional. A control module interface (not shown) may also be provided between biopsy device (100) and vacuum control module (400), for providing electrical and mechanical communication to biopsy device (100); as well as electrical communication with vacuum control module (400). A suitable control module is described in U.S. Non-Provisional patent application Ser. No. 12/337,814, entitled "CONTROL MODULE INTERFACE," filed on even date herewith, issued as U.S. Pat. No. 8,328,732 on Dec. 11, 2012, the disclosure of which is incorporated by reference herein. Among other components described herein, a footswitch (not shown) and/or other devices may be used to provide at least some degree of control of at least a portion of biopsy system (2). As shown in FIG. 1, conduits (200) provide communication of power (e.g., mechanical such as through a cable, electrical, pneumatic, etc.), control signals, saline, vacuum, and venting from vacuum control module (400) to biopsy device (100). Each of these components will be described in greater detail below.

I. Exemplary Probe

As shown in FIGS. 2-5, probe (102) of the present example comprises a needle portion (10) and a body portion (112). Body portion (112) comprises a cover member (114), a rear member (115), and a base member (116). A fluid level (150) is secured to cover member (114), and provides a bubble (152). A user may view the position of bubble (152) to determine whether probe (102) is substantially level. As will be explained in more detail below, tissue sample holder (302) is removably secured to rear member (115), though tissue sample holder (302) may alternatively be secured to cover member (114), base member (116), or some other component. As will also be described in greater detail below, a pair of tubes (402, 404) are coupled with probe (102) for providing fluid communication therewith.

Suitable configurations for probe (102) will be apparent to those of ordinary skill in the art in view of the teachings herein. For instance, probe (102) may be configured in accordance with any of the teachings in U.S. Pub. No. 2008/0214955, entitled "Presentation of Biopsy Sample by Biopsy Device," published Sep. 4, 2008, the disclosure of which is incorporated by reference herein. Other ways in which probe (102) may be configured are disclosed in U.S. Non-Provisional patent application Ser. No. 12/337,874, entitled "MECHANICAL TISSUE SAMPLE HOLDER INDEXING DEVICE," filed on even date herewith, issued as U.S. Pat. No. 8,622,927 on Jan. 7, 2014, the disclosure of which is incorporated by reference herein; U.S. Non-Provisional patent application Ser. No. 12/337,720, entitled "BIOPSY DEVICE WITH SLIDING CUTTER COVER," filed on even date herewith, issued as U.S. Pat. No. 7,862,518 on Jan. 4, 2011, the disclosure of which is incorporated by reference herein; or U.S. Non-Provisional patent application Ser. No. 12/337,942, entitled "TISSUE BIOPSY DEVICE WITH CENTRAL THUMBWHEEL," filed on even date herewith, published as U.S. Publication No. 2010/0160819 on Jun. 24, 2010, the disclosure of which is incorporated by reference herein. Still other ways in which probe (102) may be formed, including alternative techniques, materials, and configurations, will be apparent to those of ordinary skill in the art in view of the teachings herein.

A. Exemplary Needle

In the present example, needle portion (10) comprises an outer cannula (12) having a tip (20) and a transverse tissue receiving aperture (16) located proximate to tip (20). In the present example, tip (20) is substantially blunt or flat. For instance, cannula (12) may be introduced into a patient's breast through a separate cannula (not shown) that has a tissue piercing tip and a aperture configured to align with tissue receiving aperture (16) of outer cannula (12). Alternatively, cannula (12) may have its own tissue piercing tip (e.g., configured to penetrate tissue without requiring a high amount of force, and without requiring an opening to be preformed in the tissue prior to insertion of tip). By way of example only, cannula (12) may be configured in accordance with any of the teachings in U.S. Pub. No. 2008/0214955, entitled "Presentation of Biopsy Sample by Biopsy Device," published Sep. 4, 2008, the disclosure of which is incorporated by reference herein. Still other ways in which outer cannula (12) may be formed or configured, including alternative techniques, materials, and configurations, will be apparent to those of ordinary skill in the art in view of the teachings herein.

In the example shown in FIGS. 2-3, the interior of outer cannula (12) of the present example defines a cannula lumen (not shown) and a vacuum lumen (not shown), with a wall (not shown) separating the cannula lumen from the vacuum lumen. Such lumens may extend longitudinally along at least a portion of the length of cannula (12). In some versions, the wall (not shown) extends a substantial amount of the length of needle portion (10). In other embodiments, the wall proximally extends just past the region where the distal end of a cutter (50), which will be described below, terminates in needle portion (10). For instance, the cannula lumen may be sized and configured such that, with cutter (50) disposed therein, a gap exists between the exterior of cutter (50) and at least a portion of the interior of cannula (12). Such a gap may provide a vacuum lumen (40) along the length of cannula (12) positioned proximate to the proximal end of the wall. Still other ways in which a vacuum lumen may be provided will be apparent to those of ordinary skill in the art in view of the teachings herein.

Yet further, a plurality of transverse openings (not shown) may be formed through the wall separating the cannula lumen from the vacuum lumen to provide fluid communication between the cannula lumen and the vacuum lumen. As will be described in greater detail below, vacuum, saline, and/or pressurized air may be communicated from the vacuum lumen to the cannula lumen via the transverse openings. Various exemplary ways in which a vacuum lumen and cannula lumen may be provided, configured, and used are disclosed in U.S. Pub. No. 2008/0214955, entitled "Presentation of Biopsy Sample by Biopsy Device," published Sep. 4, 2008, the disclosure of which is incorporated by reference herein.

A plurality of external openings (not shown) may be formed in outer cannula (12), such that the openings are in fluid communication with the vacuum lumen of outer cannula (12). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

B. Exemplary Cutter

A hollow cutter (50) is disposed within the cannula lumen of outer cannula (12) in the present example. The interior of cutter (50) defines a cutter lumen (52), such that fluid and tissue may be communicated through cutter (50) via cutter lumen (52). As will be described in greater detail below, cutter (50) is configured to rotate within the cannula lumen of outer cannula (12) and translate axially within the cannula lumen of outer cannula (12). In particular, cutter (50) is configured to sever a biopsy sample from tissue protruding through transverse aperture (16) of outer cannula (12). As will also be described in greater detail below, cutter (50) is further configured to permit severed tissue samples to be communicated proximally through cutter lumen (52). Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system (2).

Cutter (50) may be subject to various treatments or configurations in order to facilitate proximal communication of tissue samples (4) through cutter lumen (52). Suitable configurations for cutter (50) will be apparent to those of ordinary skill in the art in view of the teachings herein. For instance, cutter (50) may be configured or treated in accordance with any of the teachings in U.S. Pub. No. 2008/0214955, entitled "Presentation of Biopsy Sample by Biopsy Device," published Sep. 4, 2008, the disclosure of which is incorporated by reference herein. Still other ways in which cutter (50) may be configured or treated, including alternative techniques and materials, will be apparent to those of ordinary skill in the art in view of the teachings herein.

C. Exemplary Needle Hub

As shown in FIGS. 2-5, a needle hub (60) is secured to outer cannula (12), and comprises a thumbwheel (62). Needle hub (60) of the present example is overmolded about a proximal portion of outer cannula (12), though needle hub (60) may be formed and/or secured relative to outer cannula (12) using any other suitable techniques (e.g., set screws, adhesives, etc.). Furthermore, while needle hub (60) of the present example is formed of a plastic material, any other suitable material or combination of materials may be used.

Thumbwheel (62) is operable to rotate outer cannula (12) about its longitudinal axis, relative to cover member (114) and base member (116). For instance, thumbwheel (62) may be used to orient aperture (16) to a number of desired orientations about the longitudinal axis defined by outer cannula (12). Such multiple orientations may be desirable, by way of example only, to obtain a plurality of tissue samples from a biopsy site, without requiring the needle portion (10) to be removed from the patient during the acquisition of such a plurality of tissue samples. An illustrative example of such rotation and acquisition of multiple tissue samples is disclosed in U.S. Pat. No. 5,526,822, the disclosure of which is incorporated by reference herein. Other ways in which multiple tissue samples may be obtained at various locations will be apparent to those of ordinary skill in the art in view of the teachings herein. For instance, rotation of outer cannula (12) may be motorized or automated, using any other suitable components or techniques. As another non-exhaustive example, an entire biopsy device (100) may be rotated during acquisition of tissue samples, without necessarily removing biopsy device (100) from the patient during such rotation and tissue sample acquisition, to obtain tissue samples from various orientations about the longitudinal axis defined by outer cannula (12).

Outer cannula (12) may terminate at or within hub (60). Hub (60) may further comprise an elongate sleeve portion (not shown), extending proximally from thumbwheel (62), about a portion of the length of cutter (50). Hub (60) of the present example further includes a second thumbwheel (64) that is integral with such a sleeve portion. For instance, thumbwheel (64) may be molded unitarily with the sleeve portion (or formed separately, if desired). Thumbwheel (64) has splines in this example, and is configured to engage with a gear (264) of holster (202), such that gear (264) and thumbwheel (64) (and, e.g., outer cannula (12)) may rotate concomitantly. This proximal region of hub (60) may also include a manifold (not shown) that is configured to provide fluid communication between tube (402) and the vacuum lumen (lateral or circumferential) of outer cannula (12). In particular, the sleeve portion of hub (60) may provide fluid communication between such a manifold and vacuum lumen. Such fluid communication may be maintained despite rotation of hub (60).

In some versions, hub (60) and its various components and features are configured in accordance with any of the teachings of U.S. Non-Provisional patent application Ser. No. 12/337,942, entitled "TISSUE BIOPSY DEVICE WITH CENTRAL THUMB WHEEL," filed on even date herewith, published as U.S. Publication No. 2010/0160819 on Jun. 24, 2010, the disclosure of which is incorporated by reference herein. In other versions, hub (60) and its various components and features are configured in accordance with any of the teachings of U.S. Pub. No. 2008/0214955, entitled "Presentation of Biopsy Sample by Biopsy Device," published Sep. 4, 2008, the disclosure of which is incorporated by reference herein. Still other ways in which needle hub (60) may be formed, including alternative techniques, materials, and configurations, will be apparent to those of ordinary skill in the art in view of the teachings herein.

D. Exemplary Cutter Rotation and Translation Mechanism

Figure 5:
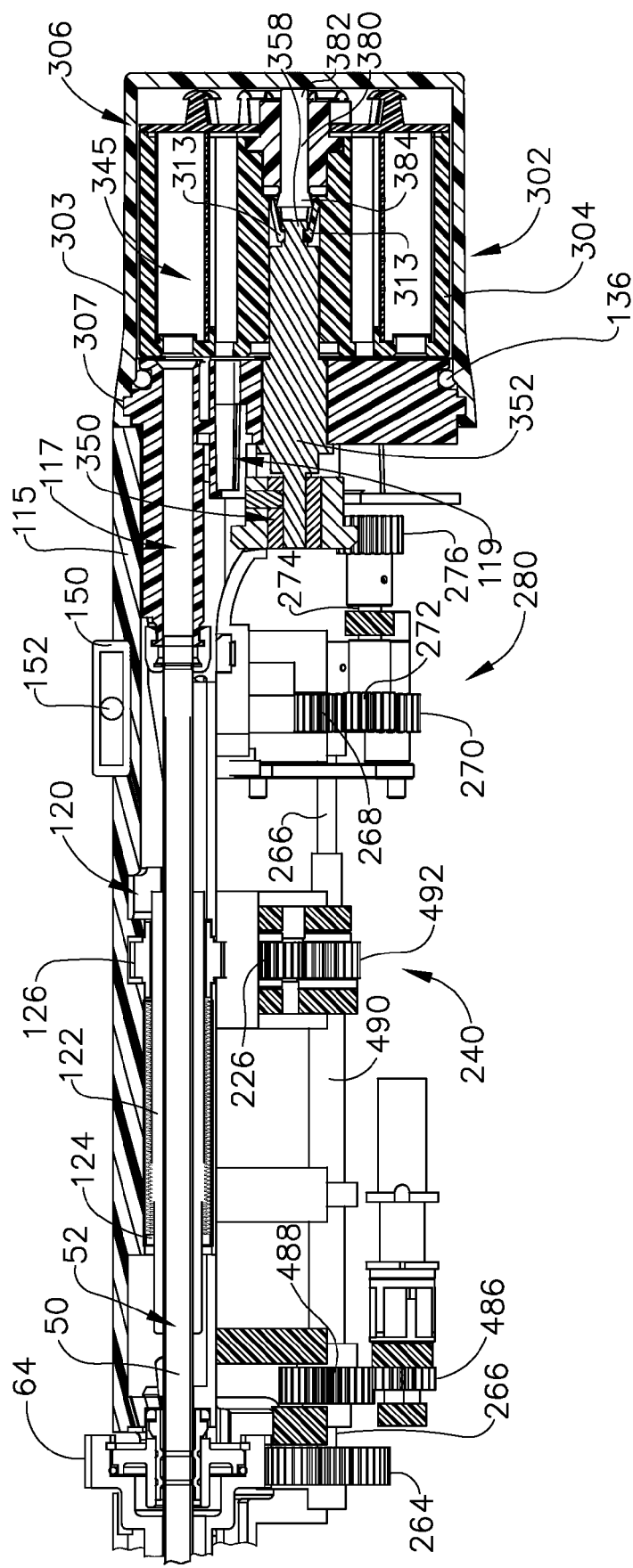
FIG. 5 is a partial, side cross-sectional view of the biopsy device of FIG. 2, showing an exemplary tissue sample holder rotation mechanism, with cutter rotation mechanism components omitted for clarity.

In the present example, and as shown in FIGS. 3 and 5, body portion (112) of probe (102) comprises a cutter rotation and translation mechanism (120), which is operable to rotate and translate cutter (50) within outer cannula (12). In particular, cutter rotation and translation mechanism (120) comprises a threaded overmold (122) fixedly secured to cutter (50); and a nut (124) with interior threading that is configured to engage threaded overmold (122). Nut (124) is fixed relative to base member (116). A splined gear (126) is positioned about overmold (122), and is configured to drivingly rotate overmold (122) while sliding relative to a hexagonal portion of overmold (122). Such components may thus be used to rotate and translate cutter (50) simultaneously upon rotation of gear (126). Of course, the hexagonal portion of overmold (122) may alternatively have a splined configuration, a keyed configuration, or any other configuration. Similarly, the complementary hexagonal interior portion of gear (126) may alternatively have a splined configuration, a keyed configuration, or any other configuration. The exterior of gear (126) may engage with cutter drive gear (226) as described in greater detail below.

Cutter rotation and translation mechanism (120) may have any other suitable components, features, or configurations. By way of example only, cutter rotation and translation mechanism (120) may be configured in accordance with any of the teachings of in U.S. Pub. No. 2008/0214955, entitled "Presentation of Biopsy Sample by Biopsy Device," published Sep. 4, 2008, the disclosure of which is incorporated by reference herein. Still other ways in which cutter rotation and translation mechanism (120) may be formed, including alternative techniques, materials, and configurations, will be apparent to those of ordinary skill in the art in view of the teachings herein.

II. Exemplary Holster

As shown in FIGS. 2-5, holster (202) of the present example comprises a housing (204), and has a drive cable (484) extending therefrom. As noted above, holster (202) of the present example is configured to be coupled with a biopsy probe (102), such as biopsy probe (102) described above, to provide a biopsy device (100). In addition, holster (202) is configured to be mounted to a table, fixture, or other device, such as for use in a stereotactic or X-ray setting; in an MRI setting; in a PEM setting; in a BSGI setting, or in an MBI setting. However, it will be appreciated in view of the disclosure herein that holster (202) may be used in a variety of other settings and combinations, including but not limited to ultrasound-guided settings and/or in handheld uses.

Figure 4:
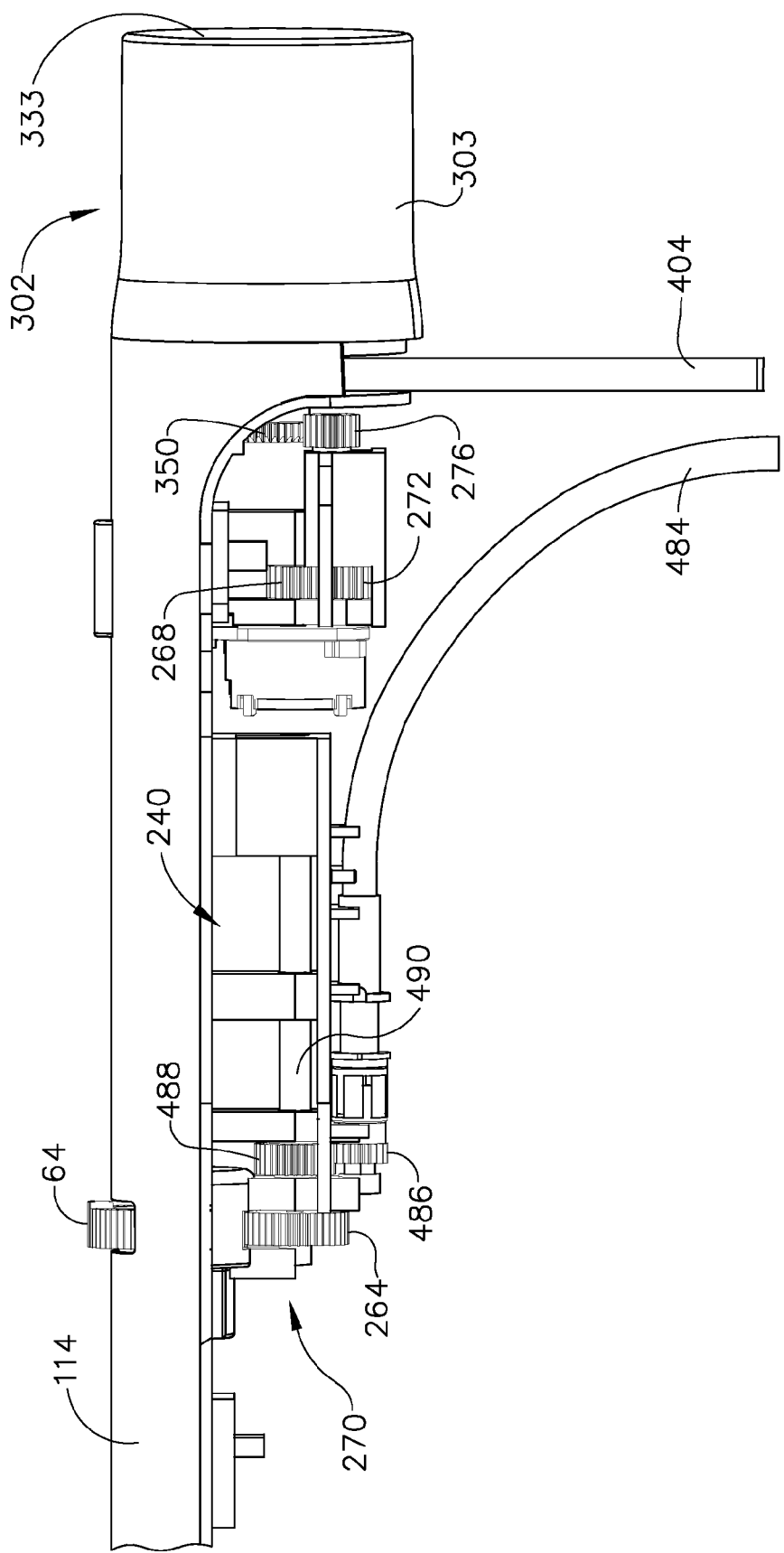
FIG. 4 is a partial side view of the biopsy device of FIG. 2, showing an exemplary tissue sample holder rotation mechanism, with a holster housing omitted for clarity.

As shown in FIG. 4, drive cable (484) is in communication with gear (486), and is thereby operable to rotate gear (486). By way of example only, drive cable (484) may be provided within and rotatable within an outer sheath. Drive cable (484) may be similar to a speedometer cable, such that rotation of cable (484) is communicated along the length of cable without significantly twisting or binding cable (484). Gear (486) may be in communication with another gear (488), which may itself be in communication with a shaft (490), such that drive cable (484), gear (486), gear (488), and shaft (490) may all rotate concomitantly, as per the gear ratio. As shown in FIG. 5, shaft (490) may be in further communication with another gear (492), such that shaft (490) may rotate gear (492). Gear (492) may be engaged with an intermittent idle gear (226), such that gear (492) may rotate gear (226) at the desired rpm and direction. As noted above, gear (226) is configured to mesh with gear (126) when probe (102) is coupled with holster (202). Accordingly, those of ordinary skill in the art will appreciate in view of the teachings herein that drive cable (484) may be used to actuate cutter rotation and translation mechanism (120), to thereby drive cutter (50). Alternatively, any other suitable components, features, or configurations may be used to drive cutter (50) (e.g., motors, etc.), to the extent that cutter (50) is driven by any mechanism at all.

As noted above, thumbwheel (64) is engaged with gear (264) when probe (102) and holster (202) are engaged in the present example. As shown in FIG. 5, gear (264) is coupled with a properly supported shaft (266), which extends through a hollow interior of shaft (490). Shaft (266) is coupled with a gear (268), which is engaged with another gear (270). This other gear (270) is engaged with yet another gear (272), which is itself engaged with a shaft (274). This shaft (274) is engaged with another gear (276). These components are thus configured such that gears (264, 268, 270, 272, 276) and shafts (266, 274) may all rotate concomitantly. All gears (264, 268, 270, 272, 276) are supported through proper bearings in this example. Gear (276) protrudes from housing (204), and is configured to engage a gear (350) of tissue sample holder (302) as will be described in greater detail below. It should therefore be understood in view of the teachings herein that rotation of thumbwheel (64) may effect concomitant rotation within tissue sample holder (302).

Other suitable components for, features of, and configurations that may be provided within holster (202) are described in U.S. Non-Provisional patent application Ser. No. 12/337,942, entitled "TISSUE BIOPSY DEVICE WITH CENTRAL THUMB WHEEL," filed on even date herewith, published as U.S. Publication No. 2010/0160819 on Jun. 24, 2010, the disclosure of which is incorporated by reference herein. Alternatively, holster (202) may be configured in accordance with any of the teachings of U.S. Pub. No. 2008/0214955, entitled "Presentation of Biopsy Sample by Biopsy Device," published Sep. 4, 2008, the disclosure of which is incorporated by reference herein. Still other ways in which the configuration of holster (202) may be formed, including alternative techniques, materials, features, components and configurations, will be apparent to those of ordinary skill in the art in view of the teachings herein.

III. Exemplary Tissue Sample Holder

Figure 6:
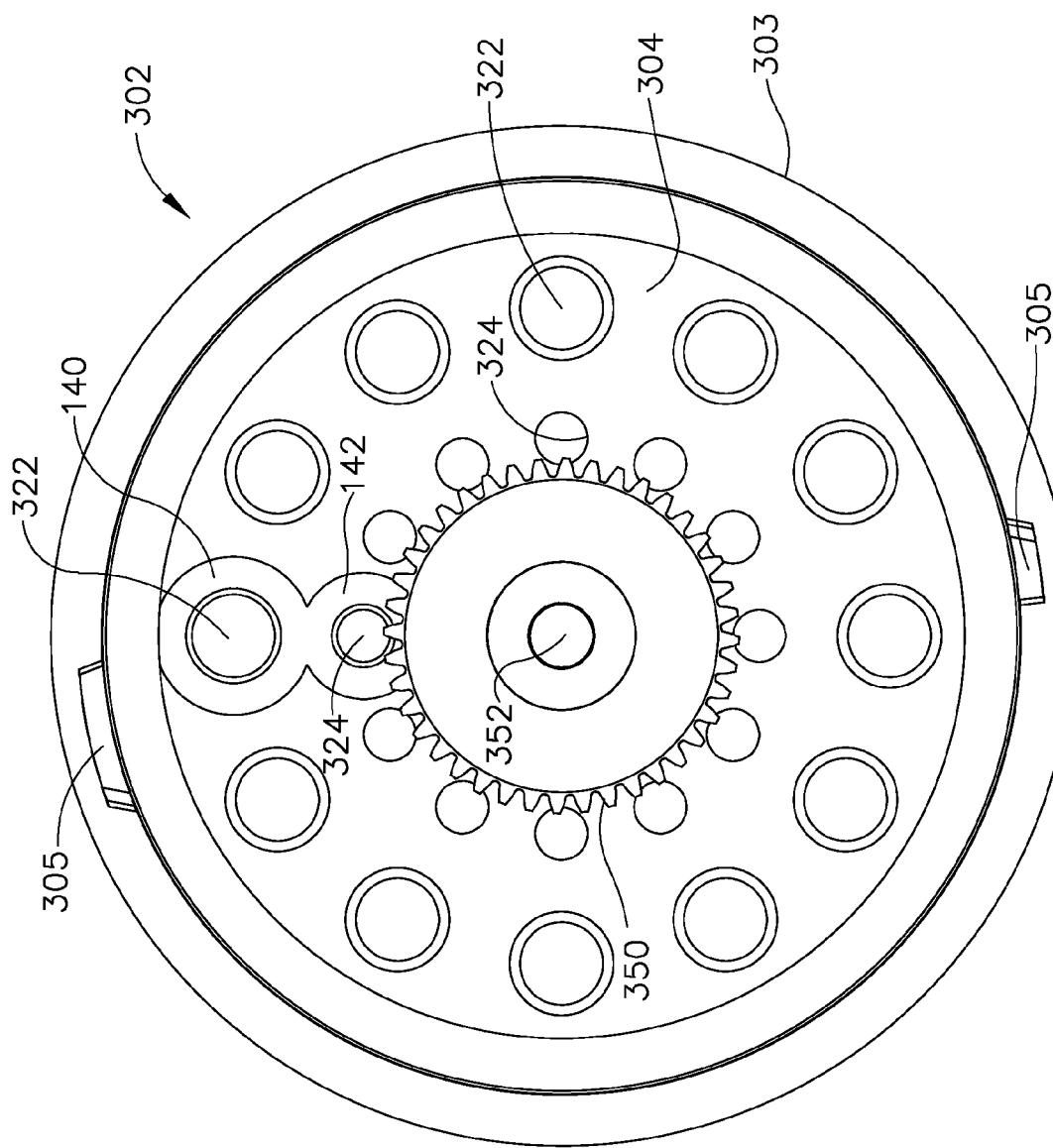
FIG. 6 is an end view of the tissue sample holder of the biopsy device of FIG. 2.
Figure 7:
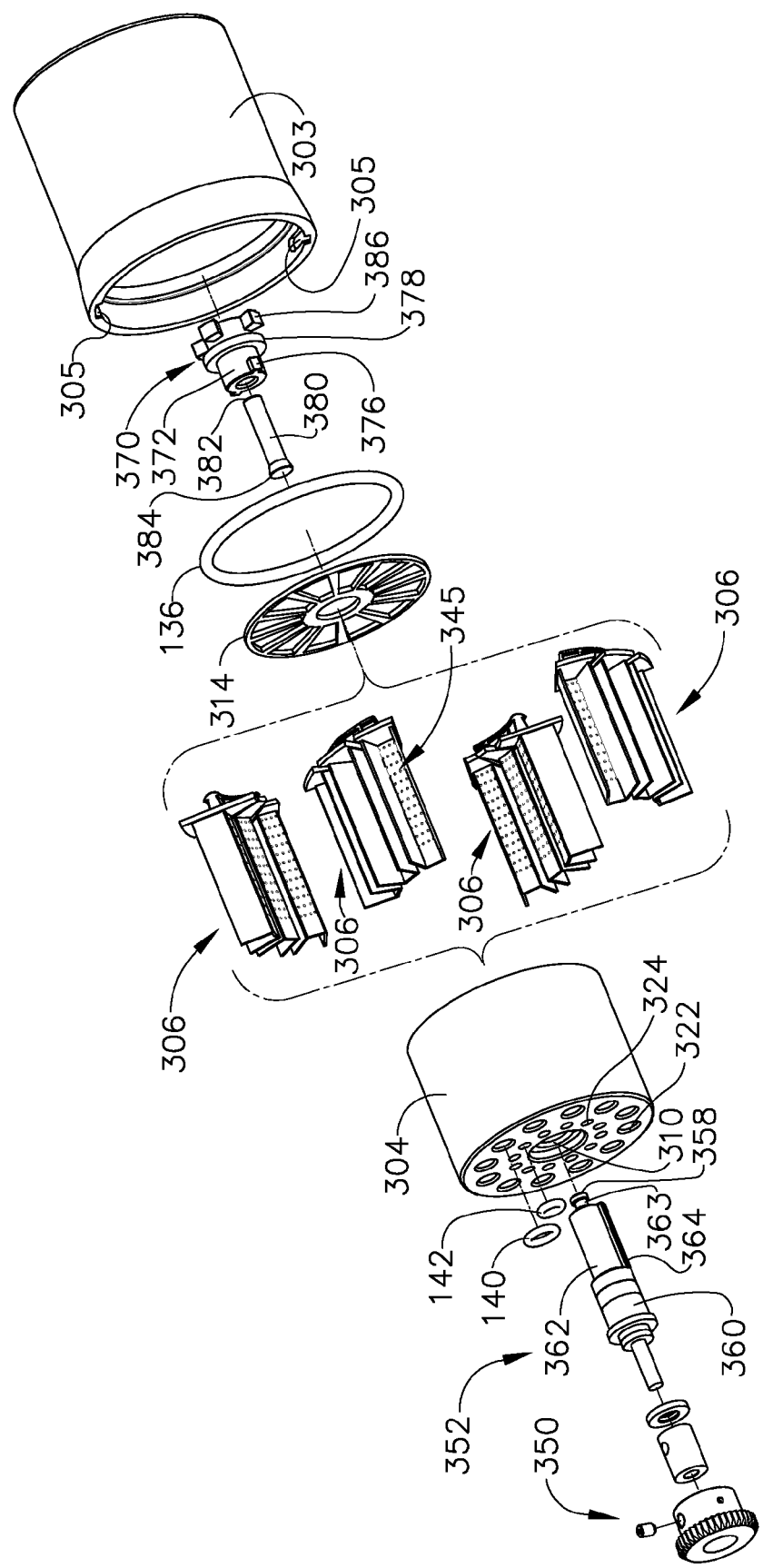
FIG. 7 is an exploded perspective view of the tissue sample holder of the biopsy device of FIG. 6.
Figure 8:
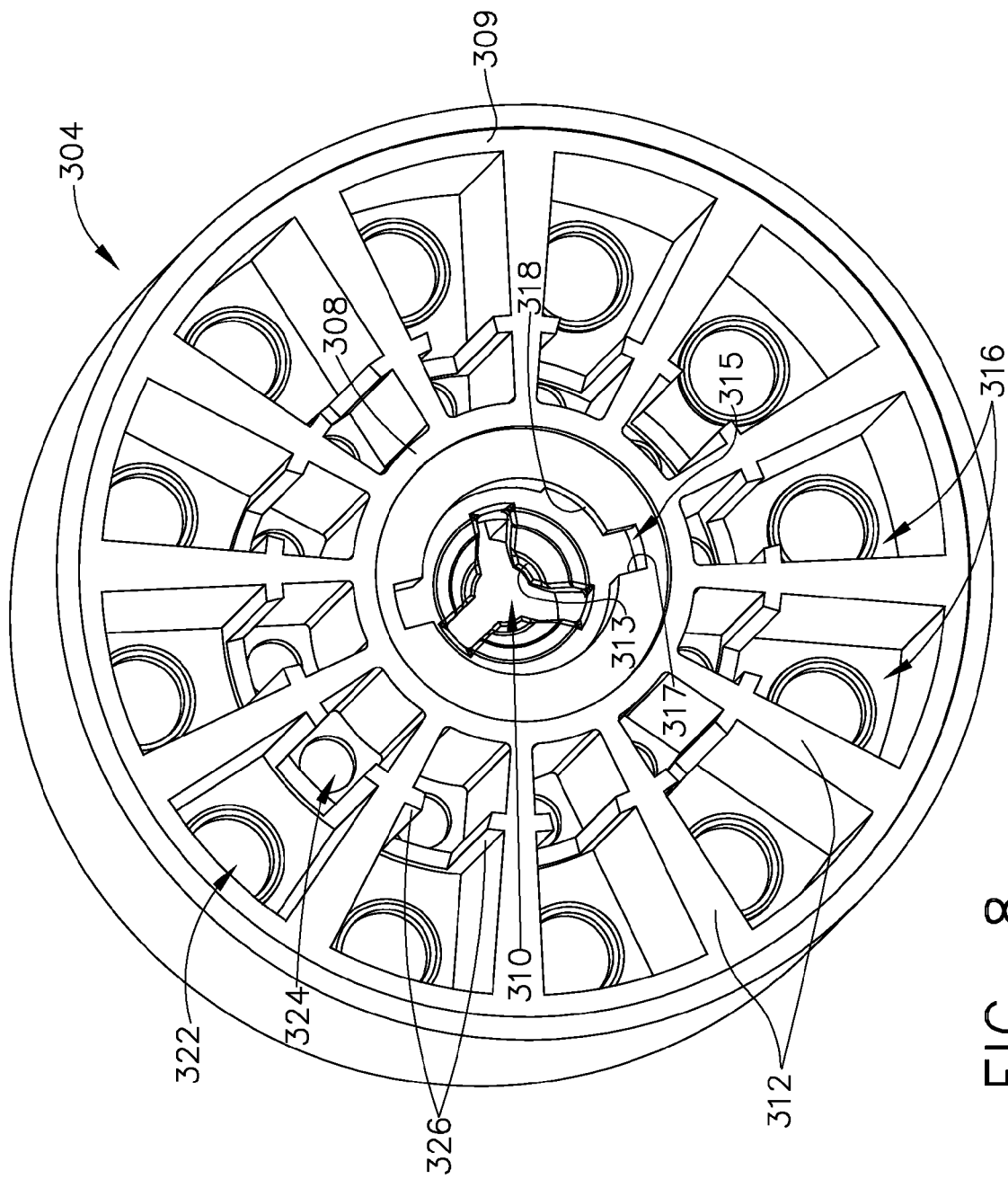
FIG. 8 is a perspective view of the housing of the tissue sample holder of FIG. 6.
Figure 9A:
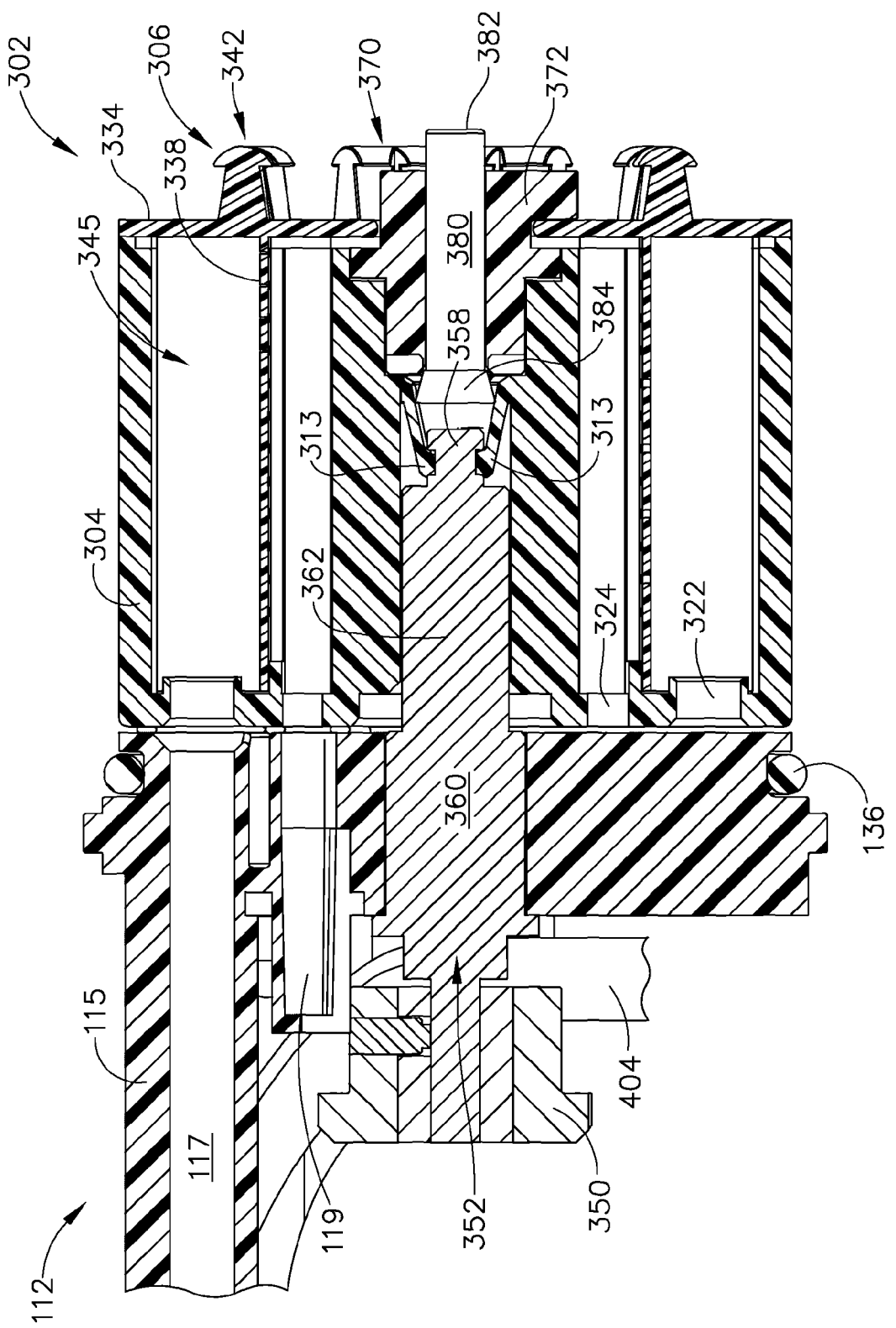
FIGS. 9A through 9C are partial, side cross-sectional views of the tissue sample holder of FIG. 6, showing a series where the tissue sample holder is selectively disengaged from the probe portion of the biopsy device.
Figure 9B:
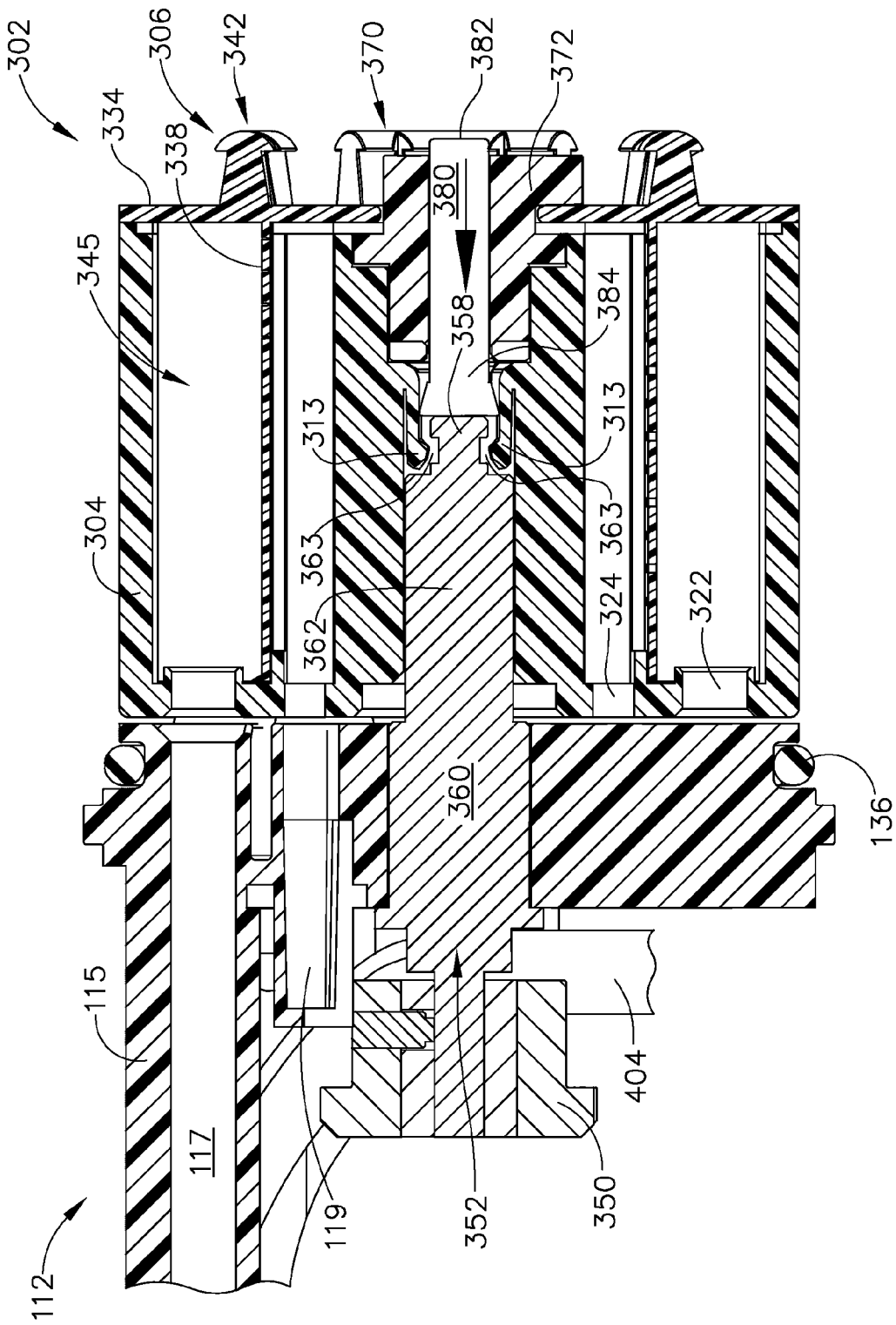
Figure 9C:
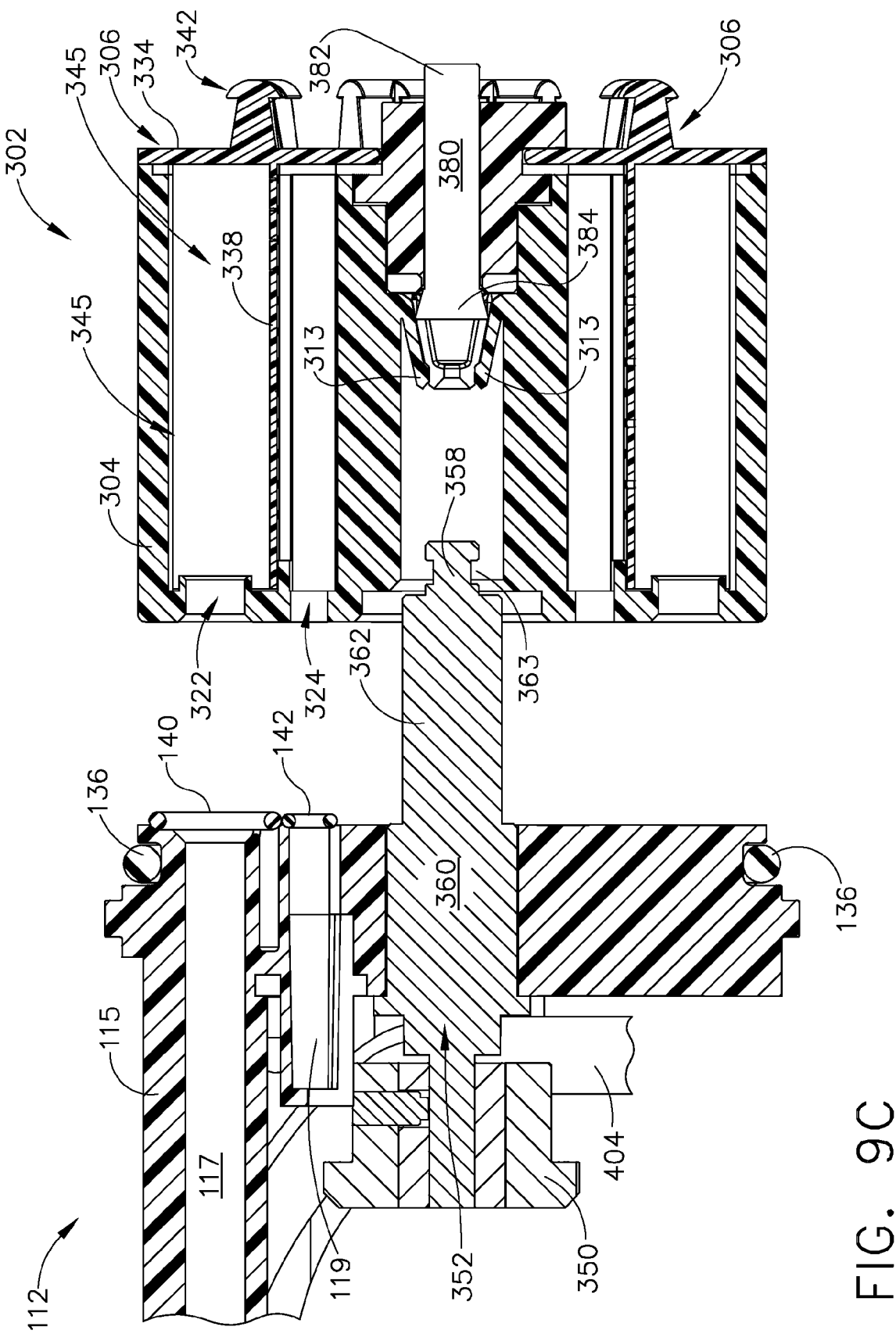

FIGS. 6-8 depict exemplary components of a tissue sample holder (302). Tissue sample holder (302) is configured to selectively engage with body portion (112) of probe (102), as shown in FIGS. 9A-9C. As shown using an exploded view in FIG. 7, tissue sample holder (302) comprises an outer cup (303) and an interior housing (304). Housing (304) is configured to receive a plurality of removable trays (306), each of which defines a plurality of tissue sample chambers (345). As will be described in greater detail below, each tissue sample chamber (345) is configured to receive at least one tissue sample captured by cutter (50) and communicated proximally through cutter lumen (52). A gear (350) is provided for rotation of housing (304), to successively index any of the tissue sample chambers (345) to cutter lumen (52), such as by manually rotating internally engaged thumbwheel (64).

A. Outer Cup

In the present example, outer cup (303) has a cylindrical shape defining a distal end and a proximal end, though any other suitable shapes or configurations may be used. Outer cup (303) is configured to engage base member (116) in a bayonet fashion, such that outer cup (303) may be selectively removed from or secured to base member (116). More specifically, the distal end of outer cup (303) includes a plurality of slots (305) capable of engaging protrusions (307) of base member (116) upon sufficient rotation of outer cup (303) relative to base member (116). Other suitable configurations for providing selective engagement between outer cup (303) and probe (112) will be apparent to those skilled in the art in view of the teachings herein. In addition, an o-ring (136) is provided about base member (116) to provide a seal between base member (116) and cup (303). Of course, any other suitable structures may be used to provide a seal between base member (116) and cup (303). Cup (303) is configured to cover interior housing (304), such that rotating or indexing interior housing (304) will not rub against any external object. In particular, cup (303) remains stationary while housing (304) rotates within cup (303). Cup (303) may also provide additional sealing for tissue sample holder (302) as a whole. It should be understood, however, that like other components described herein, cup (303) is merely optional and may be omitted or varied in a number of ways if desired.

Cup (303) of the present example is formed of a transparent material, enabling the user to visually inspect tissue samples in tissue sample holder (302) while tissue sample holder (302) is still coupled with base member (116). For instance, a user may inspect tissue samples for color, size, and density (e.g., to the extent that a chamber (316, 345) is full of saline, etc.). Alternatively, cup (303) may be translucent; opaque; a combination of translucent, opaque, and/or transparent; or have any other desired properties. For instance, a translucent cup (303) may prevent a patient from seeing blood in a tissue sample chamber (345).

In the present example, as shown in FIG. 4, cup (303) has a rear face (333). In other versions, cup (303) lacks rear face (333), such that cup (303) provides a shroud over housing (304) while permitting trays (306) to be removed from housing (304) without having to first remove cup (303). Still other ways in which cup (303) may be configured and used will be apparent to those of ordinary skill in the art in view of the teachings herein.

B. Interior Housing

As shown in FIGS. 6-8, outer cup (303) surrounds interior housing (304) of tissue sample holder (302). Housing (304) has a cylindrical shape and comprises an inner annular portion (308), which forms a central bore (310); and a plurality of radially extending walls (312) extending from inner annular portion (308) toward an outer annular portion (309). Inner annular portion (308) further includes a keyway extending axially along the inner surface of central bore (310), from its distal end toward its proximal end. The term "proximal end" when used in this context references the end of housing (304) into which trays (306) are inserted; while the term "distal end" when used in this context refers to the end of housing (304) that faces base member (116) of probe (102).

In the present example, and as shown in FIGS. 8 and 9A-9C, a plurality of resilient tabs (313) are located in central bore (310). Tabs (313) extend from the inner surface of inner annular portion (308) in a distal and radially inward direction and are configured to selectively engage shaft (352) as will be described in greater detail below. As shown in FIGS. 9A-9C, central bore (310) further defines a multi-stage cylinder having different diameters along different stages of its length. However, central bore (310) may alternatively have any suitable shape, size, features, or configuration.

As shown in FIGS. 5-7 and 9A-9C, central bore (310) is configured to receive shaft (352). As shown in FIGS. 7 and 9A-9C, shaft (352) has a first length portion (360) (e.g., a bearing portion); and a second length portion (362) (e.g., a housing engaging portion). Shaft (352) is rotatably secured within rear member (115) of probe (102). In particular, first length portion (360) is secured within rear member (115) of probe (102); while second length portion (362) protrudes rearwardly from rear member (115) of probe (102). Second length portion (362) includes an elongate key (364) that is configured to engage the keyway (not shown) of central bore (310), such that housing (304) will rotate unitarily with shaft (352). By way of example only, shaft (352) may be received by housing (304) by first aligning shaft (352) with central bore (310) such that key (364) engages the keyway (not shown) in central bore (310) upon shaft (352) entering central bore (310). Shaft (352) is configured to advance axially along central bore (310) until second length portion (362) and key (364) are substantially surrounded by central bore (310). Alternatively, shaft (352) may be secured relative to housing (304) in any other suitable fashion.

Shaft (352) of this example includes a distal end configured to engage gear (350). Gear (350) is configured to rotate unitarily with shaft (352). Accordingly, it should be understood that gear (350) rotates unitarily with housing (304) in the present example. Furthermore, as noted above, gear (350) is configured to engage with gear (276) when probe (102) is coupled with holster (202). It will therefore be appreciated in view of the teachings herein that housing (304) and thumbwheel (64) may rotate concomitantly. For instance, a user may effect rotation of housing (304) by rotating thumbwheel (64). Alternatively, a user may effect rotation of needle portion (10) by rotating housing (304). Of course, any of these components may be modified in any suitable way, and may have any other desired relationships with one another (e.g., no relationships at all, etc.).

Shaft (352) of the present example also has a proximal end having a head (358). Head (358) includes an annular recess (363). In the present example, and as illustrated in FIGS. 9A-9C, the engagement between shaft (352) and tissue sample holder (302) is secured by the use of tabs (313) in central bore (310). Tabs (313) are configured to flex outwardly when initially contacted by head (358). This movement by tabs (313) allows head (358) to continue traveling in an axial direction along central bore (310). As shown in FIG. 9A, tabs (313) resiliently move back inwardly towards a relaxed state and protrude into annular recess (363) of head (358) when inner shaft (362) is sufficiently inserted in central bore (310). Tabs (313) then grip head (358), thereby securing housing (304) to shaft (352).

The engagement between tabs (313) and annular recess (363) may be terminated by exerting a force on tabs (313) that directs tabs (313) to move outward and away from annular recess (363). For instance, as shown in FIGS. 5, 7, and 9A-9C, tissue sample holder (302) may further include a shaft (380) that provides a button (382) on one end and a flared head (384) on the other end. Shaft (380) is slidingly positioned within a tray retainer (370), which will be described in greater detail below.

As shown in FIG. 9A, button (382) projects rearwardly from tray retainer (370) when shaft (380) is in a relaxed state (e.g., when housing (304) is secured to shaft (352)). As shown, tabs (313) grip head (358) of shaft (352) by projecting into annular recess (363) of shaft (352) in this state. Furthermore, tabs (313) are engaged with flared head (384), such that the resilience of tabs (313) urge flared head (384) rearwardly; while tray retainer (370) restricts rearward movement of shaft (380) due to engagement between flared head (384) and tray retainer (370).

In an active state as shown in FIG. 9B, an operator may pull back on housing (304) while advancing or pushing button (382) axially inward (as indicated by the arrow in FIG. 9B), such that flared head (384) urges tabs (313) radially outward. Shaft (380) may be spring loaded, such that shaft (380) is biased axially rearwardly. As tabs (313) move outwardly, tabs (313) disengage annular recess (363) of shaft (352). Sufficient urging of flared head (384) toward probe (102) may flex tabs (313) outwardly enough such that tabs (313) define an inner diameter that is greater than the outer diameter of head (358). In other words, tabs (313) may be flexed outwardly enough by flared head (384) to provide sufficient clearance for head (358). Such clearance may permit disengagement of housing (304) from shaft (352), thereby permitting housing (304) to be removed from probe (102) as shown in FIG. 9C.

Of course, there are a variety of other structures, features, components devices, and techniques that may be used to provide selective engagement between housing (304) and shaft (352) (and/or between any other component of tissue sample holder (302) and probe (102)). Such alternatives will be apparent to those of ordinary skill in the art in view of the teachings herein.

As shown in FIG. 8, radially extending walls (312) of housing (304) define a plurality of chambers (316). Each chamber (316) has a proximal end and a distal end. As shown in this example, housing (304) has twelve chambers (316). However, housing (304) may have any other suitable number of chambers (316). The proximal end of each chamber (316) is configured to receive a portion of tray (306). The distal end of each chamber (316) is generally enclosed aside from an upper aperture (322) and a lower aperture (324) formed therethrough. When holder (302) and probe (102) are engaged, upper aperture (322) and lower aperture (324) of the chamber (316) that is located in the "12 o'clock position" are configured to respectively self-align with an upper o-ring (140) and a lower o-ring (142). There are many suitable structures and techniques for providing such self-alignment, which may also provide sealed engagement between probe (102) and housing (304), as will be apparent to those of ordinary skill in the art in view of the teachings herein.

O-rings (140, 142) are configured to provide a seal between rear member (115) of probe (102) and apertures (322, 324). In particular, rear member (115) has a first lumen (117) that is coaxially aligned with cutter lumen (52) and in fluid communication with cutter lumen (52). O-ring (140) provides a sealing fit between aperture (322) and first lumen (117). Accordingly, aperture (322) of a chamber (316) that is located in the "12 o'clock position" will be in fluid communication with cutter lumen (52) in this example. Tissue samples that are severed by cutter (50) may thus be communicated proximally through cutter lumen (52) (due to a pressure gradient), through first lumen (117), through aperture (322), and into the chamber (316) that is located in the "12 o'clock position" in this example. Rear member (115) also has a manifold providing a second lumen (119) that is in fluid communication with tube (404). O-ring (142) provides a sealing fit between aperture (324) and second lumen (119). Accordingly, aperture (324) of a chamber (316) that is located in the "12 o'clock position" will be in fluid communication with tube (404) in this example. By way of example only, a vacuum may thus be induced in the chamber (316) that is located in the "12 o'clock position" via aperture (324), second lumen (119), and tube (404). As will be explained in greater detail below, such a vacuum may be further communicated through aperture (322), and hence through cutter lumen (52), through a apertures (344) formed in a tray (306) that is inserted in the chamber (316).

Chambers (316) may also include guide rails (326) on the surface of walls (312). Guide rails (326) extend parallel to inner annular portion (308) and on opposite walls (312) in a respective chamber (316). As will be explained in more detail below, a set of guide rails (326) in each chamber (316) engage or support tray (306) upon tray (306) being received into chambers (316). In the example of tray (306) shown in FIGS. 7 and 11-12, a single tray (306) is configured to engage three chambers (316) of housing (304), such that four trays (306) may simultaneously be supported by housing (304). Other suitable variations of tray (306) and housing (304) will be apparent to those of ordinary skill in the art. For example, and as will be discussed below with reference to FIGS. 13-14, each tray (306) may be configured to only engage a single corresponding chamber (316) within housing (304).

It should be understood that housing (304) may be configured in a variety of other ways, and that housing (304) may have a variety of other features, components, and configurations. For instance, housing (304) may alternatively be configured in accordance with any manifold or other component(s) taught in U.S. Pub. No. 2008/0214995, entitled "Presentation of Biopsy Sample by Biopsy Device," published Sep. 4, 2008, the disclosure of which is incorporated by reference herein. Housing (304) and/or cup (303) may also have knurling or other features (e.g., circumferential and/or linear) on its outer surface, for facilitating gripping of housing (304) and/or cup (303) when decoupling housing (304) and/or cup (303) from probe (102) and/or for other purposes. Still other suitable features, components, and configurations for housing (304) will be apparent to those of ordinary skill in the art in view of the teachings herein.

C. Tissue Sample Trays

As noted above, trays (306) are configured to be received by housing (304), and to receive tissue samples. More specifically, trays (306) are configured to be received in chambers (316) of housing (304). Each tray (306) may be rigid, and may be preformed to have a generally arcuate configuration. Alternatively, trays (306) may be formed of a flexible and/or resilient material, such that trays (306) may be bent to conform to the shape and size of a chamber (316), flattened out after removal from chambers (316), etc. Similarly, trays (306) may comprise one or more joints, such that portions of trays (306) may bend or flex at such joints. Still other suitable features, configurations, and properties for trays (306) will be apparent to those of ordinary skill in the art in view of the teachings herein.

Figure 11:
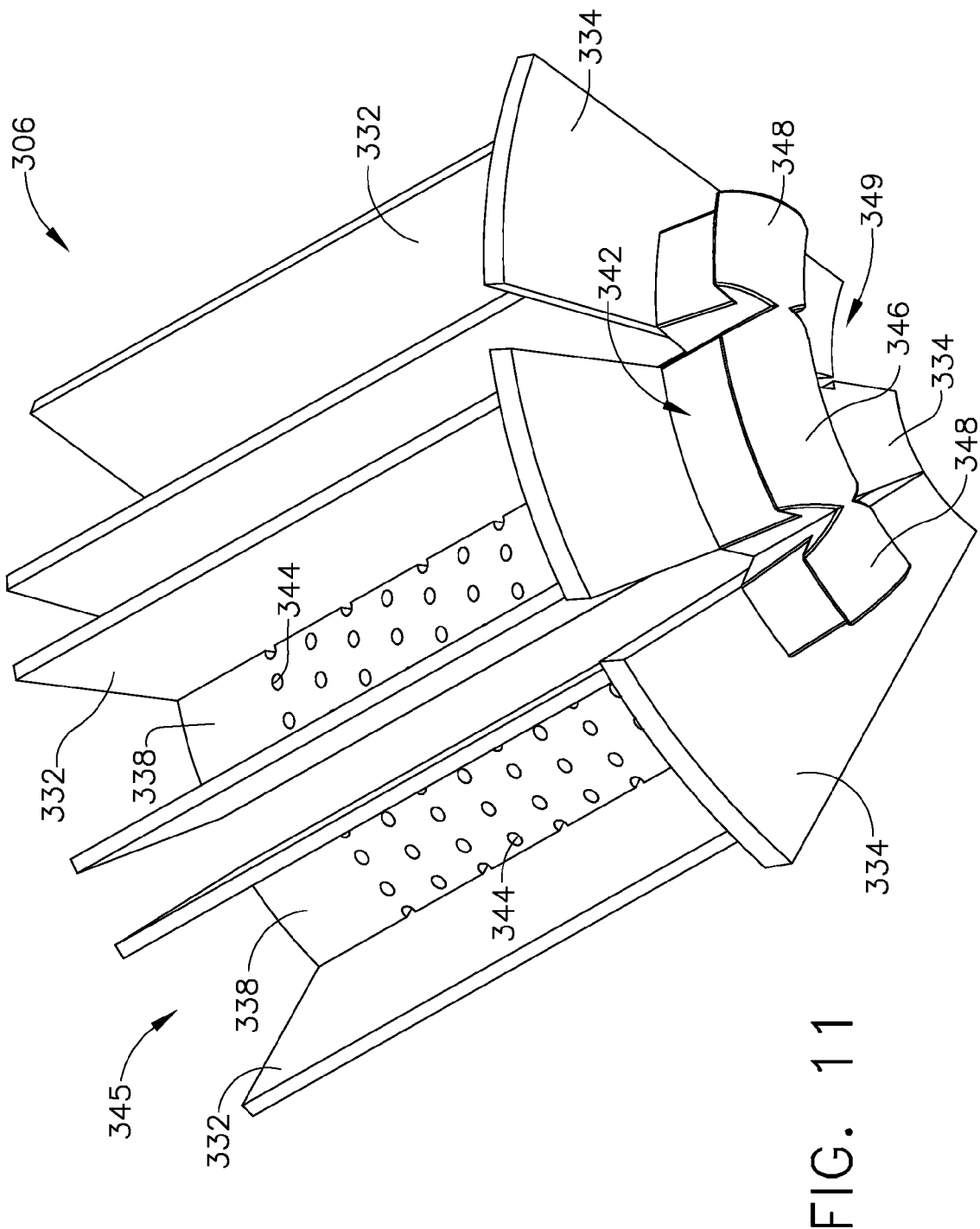
FIG. 11 is a perspective view of one of the tissue sample trays of the tissue sample holder of FIG. 6.

As shown in FIG. 11, tray (306) of the present example includes a plurality of sidewalls (332). Each pair of sidewalls (332) extends from a corresponding back wall (334). Each pair of sidewalls (332) also extends from a corresponding floor (338). A pair of adjacent sidewalls (332), back wall (334), and floor (338) together define a corresponding tissue sample chamber (345). By way of example only, and as will be described in greater detail below, each tissue sample chamber (345) may be configured to receive at least one tissue sample captured by cutter (50).

In the example shown, each sidewall (332) respectively forms a distal edge and a proximal edge. The proximal edge of each sidewall (332) is integral with a corresponding back wall (334); whereas the distal edge of each sidewall (332) is free. The distal edge of each sidewall (332) may include a plurality of recesses that are configured to engage guide rails (324) of housing (304) as tray (306) is received by housing (304). Alternatively, trays (306) may be configured such that guide rails (324) engage corners that are formed by sidewalls (332) and floors (338).

Referring still to FIG. 11, back wall (334) may extend radially outwardly past the proximal edges of corresponding sidewalls (332). Thus, sidewalls (332) and floors (338) may be capable of entering a chamber (316) by first placing the distal end of tray (306) in corresponding chambers (316), and advancing sidewalls (332) and floors (338) in a distal direction along chamber (316). Sidewalls (332) may then only extend into chamber (316) for the length of sidewalls (332) and/or until back wall (334) engages the rear face of housing (304).

In addition, as shown in FIG. 7, a soft silicone gasket (314) may be positioned at the rear face of housing (304), to provide a sealed fit between back walls (334) and housing (304). Gasket (314) of the present example has a circular shape that generally defines an outer circular surface and an inner circular surface connected by a series of webbing. The web of gasket (314) forms a plurality of apertures that correspond with chambers (316). The formation of the web allows gasket (314) to conform to the shape of the proximal end of housing (304). More particularly, gasket (314) when positioned proximate to the proximal end of housing (304) may be aligned such that each aperture formed by the web may align with a respective chamber (316) of housing (304). In the example shown, the web of gasket (314) forms twelve apertures such that each aperture may be respectively aligned with one of the twelve chambers (316) of housing (304). In some other versions, gasket (304) is overmolded on the face of housing (304), such as with a soft plastic or elastomer to obtain a seal. Other suitable configurations of gasket (314) will be apparent to those skilled in the art. Alternatively, as with other components described herein, gasket (314) may simply be omitted altogether.

In the example shown in FIG. 11, back walls (334) of tray (306) also include a flexible handling member (342). Flexible handling member (342) may be grasped and used by an operator to otherwise handle tray (306), direct tray (306) to enter chamber (316), and/or remove tray (306) from chamber (316). It will be understood by those skilled in the art that flexible handling member (342) may be provided in any suitable size or shape. For example, flexible handling member (342) may have a square or round shape. Flexible handling member (342) shown in this example includes a central portion (346) extending from a back wall (334) and coupled to two end portions (348), each of which also extends from a corresponding back wall (334). In this example, central portion (346) is respectively connected to each end portion (348) along respective edges. The intersections of these edges respectively form axes around which portions (346, 348) may hingedly rotate. In other words, handling member (342) of this example defines a pair of living hinges, each hinge being positioned between central portion (346) and end portions (348). Tray (306) is thus capable of being configured in a flat position. Having the ability to maneuver or otherwise handle a tray (306) in such a manner may be helpful when attempting to access a tissue sample residing in a tissue sample chamber (345). Having this ability may also be convenient for cleaning a tray (306), for laying tray (306) flat to examine tissue samples therein, and/or for a variety of other purposes.

As shown in this example, each floor (338) includes a plurality of apertures (344) formed therethrough. Apertures (344) may be of any suitable shape and size. For example, apertures (344) may have a circular shape or an elongated shape (e.g., slots, etc.). Likewise, different sized and shaped apertures (344) may be provided within each floor (338). Generally, apertures (344) have a size large enough to allow blood, saline, and/or other fluids to pass through tissue sample chamber (345) into chamber (316), and exit through tube (404) via aperture (324), even if a tissue sample is within such a tissue sample chamber (345). Thus, in some examples, apertures (344) are generally not large enough to allow a tissue sample to travel therethrough. Of course, apertures (344) may be located elsewhere on tray (306) or have any other desired configuration or utility. It should be understood that apertures (344) of the present example provide a path for fluid communication from aperture (322) to aperture (324) when tray (306) is inserted in chamber (316). Referring back to an example described above, a vacuum from tube (404) may be communicated from aperture (324) through aperture (322) (and, hence, through cutter lumen (52)) via apertures (324) of the tray (306) that is in the "12 o'clock position."

During operation of biopsy system (2), tray (306) is configured to be insertingly positioned in a chamber (316). More particularly, tray (306) may be configured such that the distal end of floor (338) is partly positioned between apertures (322, 324) when tray (306) is inserted in chambers (316). For example, tray (306) may be configured such that floor (338) is located below aperture (322) and above aperture (324) as shown in FIG. 9A. In this configuration, any air, gas, liquid, or other matter capable of passing through apertures (344) of floor (338) may travel through first lumen (117) of probe (102) and into tray (306) via upper aperture (322); then exit tray (306) by traveling through lower aperture (324) then through second lumen (119) and tube (404). Further, as noted above in the discussion of o-rings (140, 142), probe (102) and tissue sample holder (302) may be configured such that the engagement between the two creates a hermetic seal for the respective chamber (316) that is aligned proximate to the first lumen (117) and second lumen (119). This hermetic seal may be enhanced or otherwise provided by using a spring (not shown) in a tissue sample holder engaging mechanism. In the present example, this position where aperture (322) aligns with lumen (117), and where aperture (324) aligns with lumen (119), is otherwise referred to as the "12 o'clock position."

As shown in FIG. 11, a back wall (334) of a tray (306) may be configured to include a notch (349). Such a notch (349) may be configured to allow tray (306) to be advanced in and out of a chamber (316) while tray retainer (370) is engaged with housing (304). As seen in FIGS. 10A and 10B, and as will be discussed in greater detail below, notch (349) is located at a bottom edge of one back wall (334) of tray (306).

A tray retainer (370) is configured to secure the engagement between a tray (306) and housing (304). As shown in FIG. 7, tray retainer (370) of the present example includes a shaft (372) having locking members (376) at a distal end and radial projections (386) at a proximal end. An annular flange (378) surrounds a portion of shaft (372) between radial projections (386) and locking members (376). Annular flange (386) has a diameter that is greater than the diameter of central bore (310) of housing (304) in this example. Shaft (380) described above is slidingly positioned within shaft (372) of tray retainer (370), such that button (382) protrudes rearwardly from the rear face of tray retainer (370).

Tray retainer (370) is removably engaged with housing (304). In particular, inner annular portion (308) of housing (304) defines a plurality of recesses (315) at its proximal end. As shown in FIG. 8, each recess (315) has a first stage (317) that provides clearance in an axial direction along the inner surface of inner annular portion (308); and a second stage (318) that is directed annularly along the inner surface of inner annular portion (308). Locking members (376) are configured to engage with recesses (315). In particular, tray retainer (370) engages housing (304) by first positioning the distal end of shaft (372) having locking members (376) into central bore (310). Initially, locking members (376) travel axially along the first stage of recesses (315). However, locking members (376) are prevented from traveling any further axially once annular flange (378) abuts housing (304). Locking members (376) may then be advanced along the second stage of recesses (315) in an angular direction. Rotatingly advancing locking members (376) in such a fashion prevents axial movement of tray retainer (370) without reversing the path of locking members (376). Of course, tray retainer (370) may be secured to housing in any other suitable fashion.

As shown in FIG. 10A, tray retainer (370) may positioned in relation to recess (349) such that tray retainer (370) prevents trays (306) from being removed from housing (304). In particular, radial projections (386) may prevent rearward movement of back walls (334), thereby "locking" trays (306) into housing (304). Tray retainer (370) may be rotated, for example in the direction of the arrow shown in FIG. 10A, and positioned as shown in FIG. 10B, to allow trays (306) to be respectively advanced in and out of chambers (316). For instance, as shown in FIG. 10B, tray retainer (370) may be rotated such that radial projections (386) correspond with notches (349) in trays (306). Radial projections (386) and notches (349) may be configured such that aligning these two features provides sufficient clearance for an operator to pull trays (306) rearwardly out of housing (304) (e.g., such as by gripping handling members (342)). Such a rotational position of tray retainer (370) may also permit trays (306) to be inserted into housing (304). Of course, a variety of alternative features, components, structures, devices, configurations, and techniques may be used to selectively secure the position of trays (306) in housing (304).

In use, an operator may remove a tray (306) while needle portion (10) is still inserted in a patient. With respect to a chamber (316) that is located at the "12 o'clock position," the operator may insert the cannula of a biopsy site marking device from the rear of probe (102), through aperture (322), through cutter lumen (52), to deploy a biopsy site marker through aperture (16). Suitable devices for deploying such biopsy site markers are known in the art. To the extent that the rotational position of housing (304) is indexed to the rotational position of needle portion (10) as described above, various markers may be deployed at various rotational positions about the axis defined by needle portion (10), simply by reintroducing the marker device through probe (102) as described above for each rotational position desired.

Each tray (306) and/or chamber (316) may respectively comprise one or more types of markings or other indicia to distinguish one tray (306) or chamber (316) from another tray (306) or chamber (316). For instance, a number or other distinguishing marking may be provided on or near each tray (306) or chamber (316), such as in relief form, in recessed form, or otherwise. In another embodiment, a radiopaque marker is provided on or near each tray (306). By way of example only, a marker that is both visible to the naked eye and radiopaque may be integrated directly into handling member (342) or any other portion of tray (306). A tray (306) that is carrying at least one tissue sample may be placed under X-ray for evaluation, and the radiopaque marker associated with each tissue sample chamber (345) (and hence, associated with each tissue sample), may be visible in the image obtained using X-ray. In other words, tissue samples need not necessarily be removed from trays (306) in order to take an X-ray or radiograph image of tissue samples. Furthermore, trays (306) may be dropped directly into formalin or any other liquid with tissue samples still on trays (306). In addition, trays (306) may be placed in a sleeve or container, etc., individually or in groups, to protect tissue samples and/or to ensure that tissue samples stay in trays (306) or for other purposes. Such a sleeve or container may be flexible, rigid, or have other properties. By way of example only, a sleeve or other container may be flat, and may be configured to flatten out a flexible tray (306) that is inserted therein. Other structures and techniques that may be used with trays (306), such as after tissue samples are communicated to trays (306) will be apparent to those of ordinary skill in the art in view of the teachings herein.

It should be understood that the features and configurations of tray (306) described herein are merely exemplary, and that any suitable alternatives may be used. For instance, non-exhaustive examples of other configurations of trays are shown in FIGS. 12-15 and are described below. Other suitable features, configurations, treatments, or materials for tray (306) will be apparent to those of ordinary skill in the art in view of the teachings herein.

Figure 12:
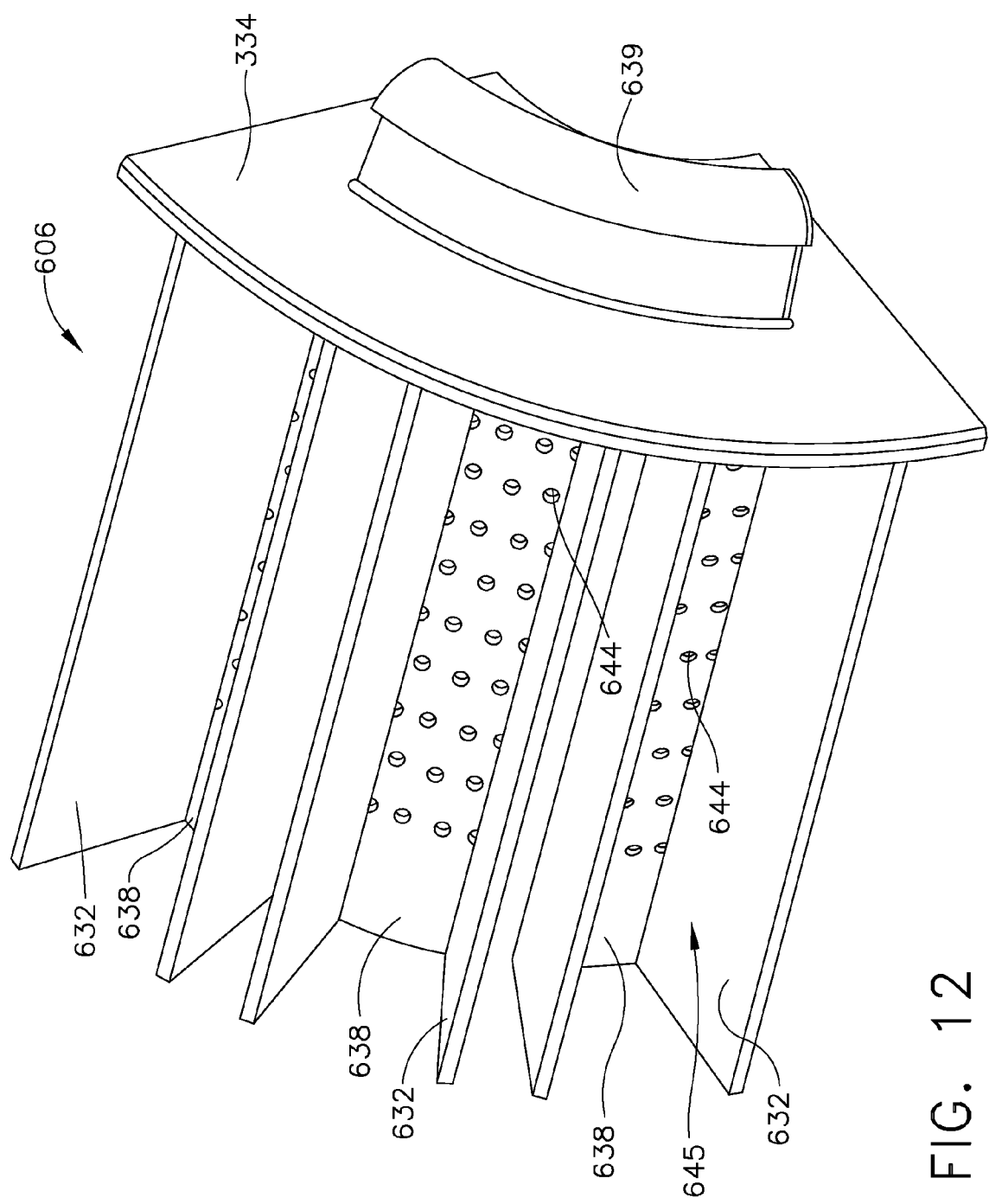
FIG. 12 is a perspective view of a merely exemplary alternative tissue sample tray.

As shown in FIG. 12, an alternative tray (606) is depicted that may be used in conjunction with tissue sample holder (302) in the same manner as tray (306). Similar to tray (306), tray (606) comprises a plurality of sidewalls (632) respectively connected to single back wall (334). Each pair of sidewalls (632) is also connected to a corresponding floor (638). Sidewalls (632), floors (638), and back wall (334) thus together define tissue sample chambers (645). Each floor (638) has a plurality of apertures (644) formed therethrough, much like apertures (344) described above. Tray (606) further includes a handling member (639). In this example, handling member (639) comprises a rigid member attached to back wall (334). The rigidity of back wall (334) and handling member (639) substantially prevents re-positioning of tissue sample chambers (645) relative to each other. However, sidewalls (632) and/or floors (638) may otherwise have some degree of flexibility if desired. Further, back wall (334) and handling member (639) may also have some degree of flexibility if desired.

Tray (606) may be used in a manner similar to that described above with respect to tray (306). For example, tray (606) may be axially advanced into a housing (304) such that a respective tissue sample chamber (645) is respectively advanced into a chamber (316) of housing (304). In this example, tray (606) is configured to engage three chambers (316) simultaneously. Tray (606) may otherwise be configured to be locked into an engagement with a housing (304) by a tray retainer (370). Further, tray (606) may be configured to include a notch or any other suitable feature to allow tray (606) to be selectively advanced into and removed from a housing (304). Alternatively, tray (606) may selectively couple with housing (304) in any other suitable fashion.

Figure 13:
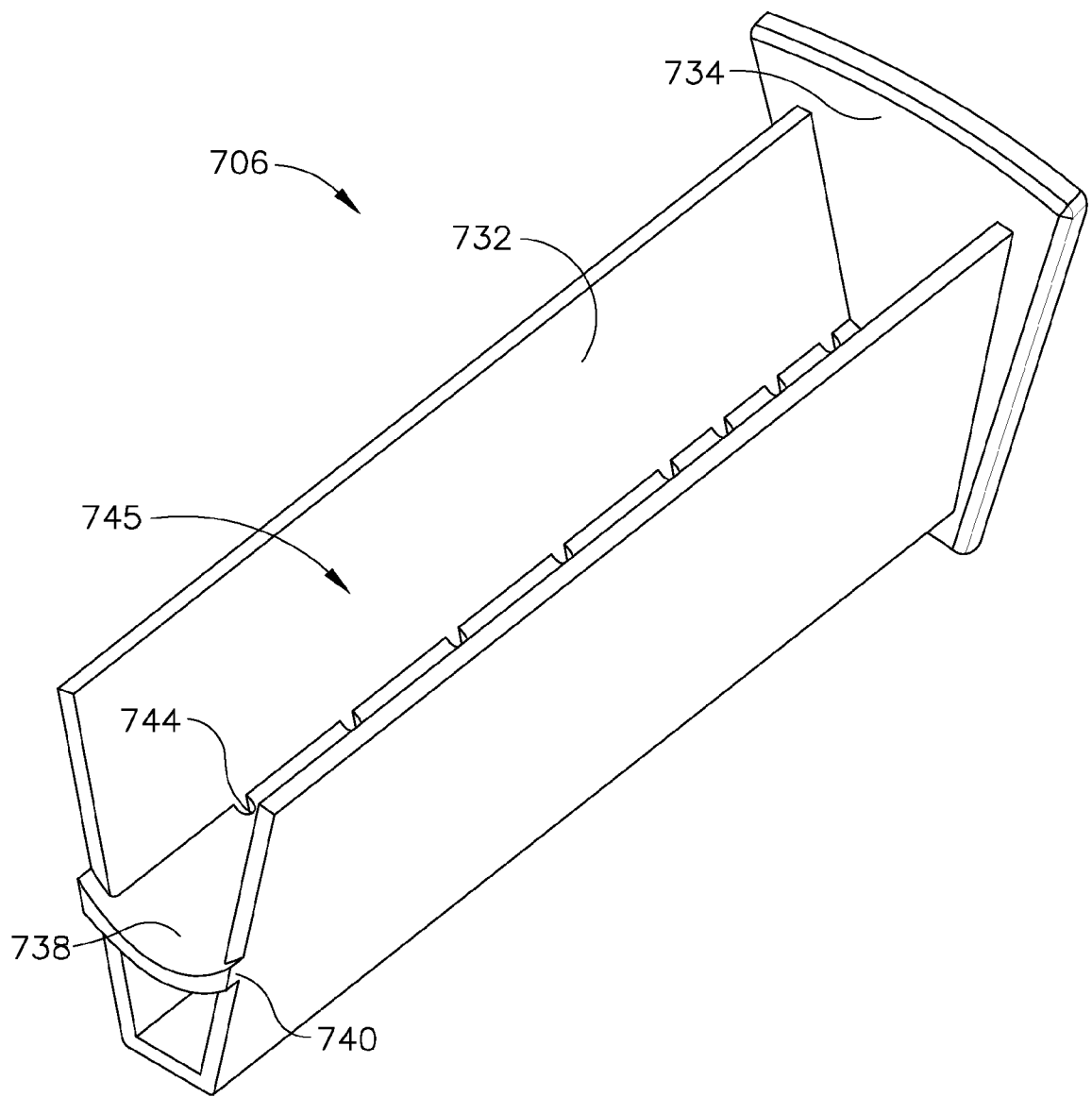
FIG. 13 is a perspective view of another merely exemplary alternative tissue sample tray.
Figure 14:
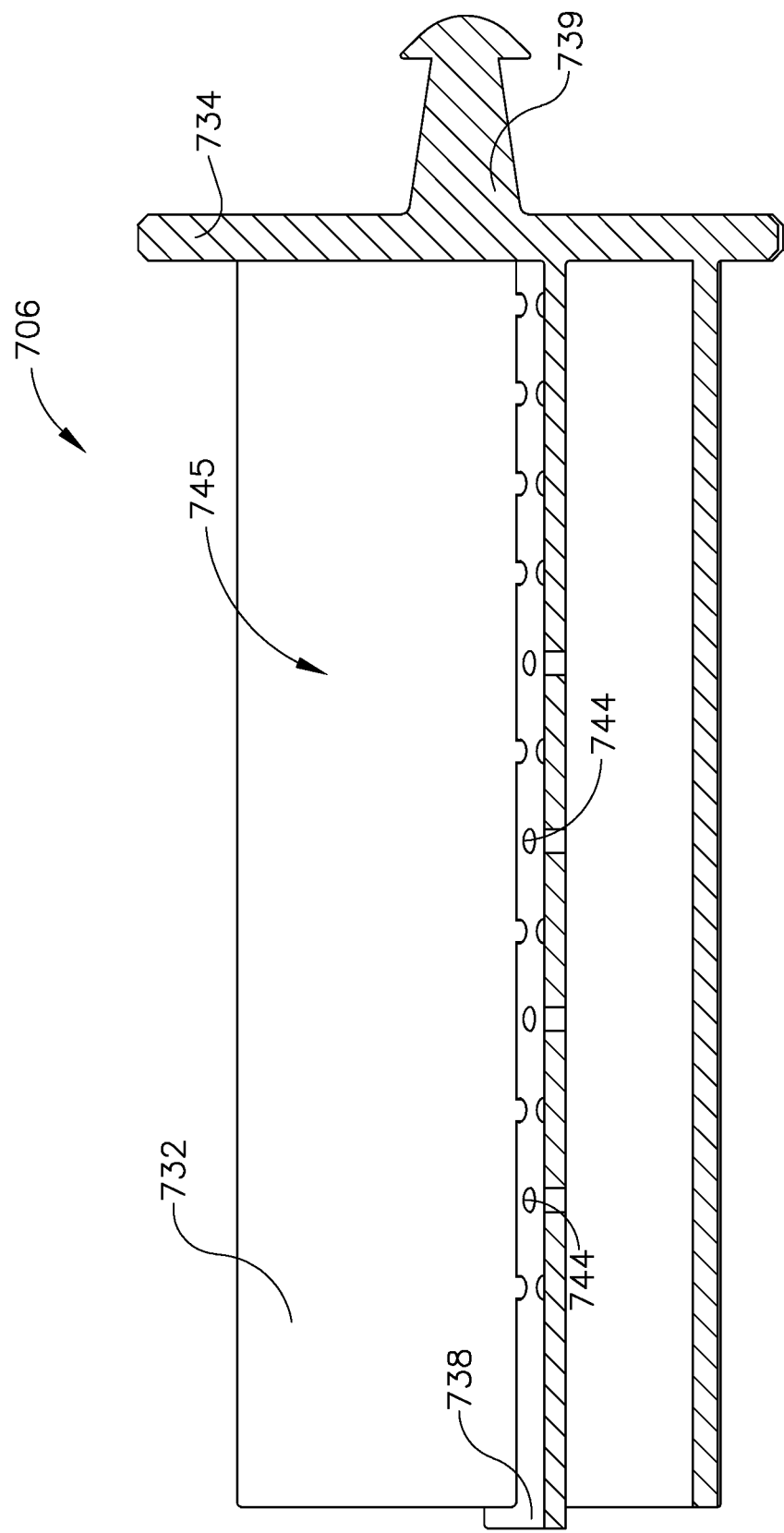
FIG. 14 is a side cross-sectional view of the tissue sample tray of FIG. 13.

FIGS. 13-14 show another alternative tray (706) comprising a single pair of sidewalls (732), a single floor (738), and a back wall (734) having a handling member (739). Sidewalls (732), floor (738), and back wall (734) together define a tissue sample chamber (745). In this example, tray (706) is configured to engage a single chamber (316) within housing (304). In the present example, housing (304) may simultaneously support twelve trays (706). Like apertures (344) in floor (338) of tray (306), floor (738) of tray (706) also includes a plurality of apertures (744).

Tray (706) may be used in a manner similar to that described above with respect to tray (306). For example, tray (706) may be axially advanced into a housing (304) such that tissue sample chamber (745) is advanced into a chamber (316) of housing (304). Tray (706) may otherwise be configured to be locked into an engagement with a housing (304) by a tray retainer (370). Further, tray (706) may be configured to include a notch or any other suitable component to selectively allow tray (706) to be advanced into and removed from a housing (304). Alternatively, tray (706) may selectively couple with housing (304) in any other suitable fashion.

Figure 15:
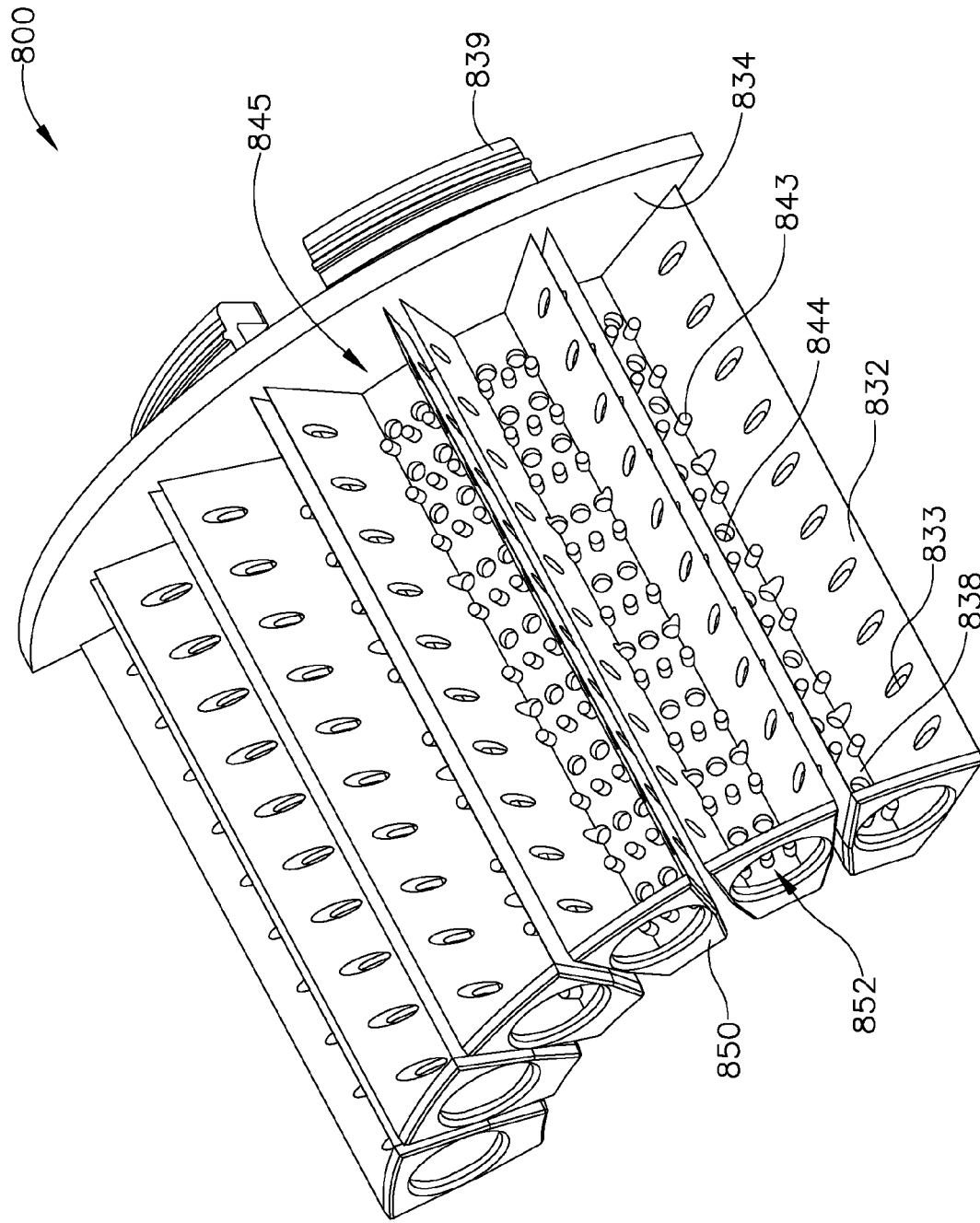
FIG. 15 is a perspective view of another merely exemplary alternative tissue sample tray.

FIG. 15 shows yet another alternative tray (800) that may be used in conjunction with tissue sample holder (302) in the same manner as tray (306). Similar to tray (306), tray (800) comprises a plurality of sidewalls (832) respectively connected to a single a back wall (834). Each pair of sidewalls (832) is also connected to a corresponding floor (838). Sidewalls (832), floors (838), and back wall (834) thus together define tissue sample chambers (845). Each floor (838) has a plurality of apertures (844) formed therethrough, much like apertures (344) described above. Tray (806) further includes a pair of handling members (839), which each comprise a rigid member attached to back wall (834) in this example. The rigidity of back wall (834) and handling members (839) may substantially prevent re-positioning of tissue sample chambers (845) relative to each other, if desired. Alternatively, back wall back wall (834) and handling members (839) may provide some degree of flexibility if desired (e.g., to permit tray (800) to be flattened out for examination or imaging of tissue samples therein, etc.).

Tray (800) of the present example also includes a plurality of apertures (833) formed through sidewalls (832), which may enhance fluid communication through tissue sample chambers (845). For instance, such apertures (833) may maintain fluid communication between lumen (117) and lumen (119), such as when such fluid communication might otherwise be hampered or prevented by a tissue sample in tissue sample chamber (845) (e.g., blocking openings (844), etc.). In addition, tray (800) of the present example includes a plurality of protrusions (843) extending upwardly from each floor (838). Such protrusions (843) may enhance fluid communication by preventing a tissue sample from blocking apertures (844) of floor (838) of the tissue sample chamber (845) that the tissue sample has been drawn into. Such protrusions (843) may also help retain the tissue sample in its chamber (845) during transport of tray (800) for testing of the tissue sample. Tray (800) of this example also includes a distal wall (850) having an aperture (852) formed therethrough. Aperture (852) may be configured to align with a corresponding upper aperture (322) of housing (304), such that tissue drawn through upper aperture (322) is also drawn through aperture (852) to reach tissue sample chamber (845). Distal wall (850) and aperture (852) may also be configured such that they reduce the likelihood of a tissue sample being left in housing (304) when tray (800) is removed from housing (304). In other words, distal wall (850) may help retain a tissue sample within tissue sample chamber (845), at least to some degree, as tray (800) is removed from housing (304) and thereafter.

Tray (800) may be used in a manner similar to that described above with respect to tray (306). For example, tray (800) may be axially advanced into a housing (304) such that a respective tissue sample chamber (845) is respectively advanced into a chamber (316) of housing (304). In this example, tray (800) is configured to engage six chambers (316) simultaneously, though tray (800) may simultaneously engage any other desired number of chambers (316). Tray (800) may otherwise be configured to be locked into an engagement with a housing (304) by a tray retainer (370). Further, tray (800) may be configured to include a notch or any other suitable feature to allow tray (800) to be selectively advanced into and removed from a housing (304). Alternatively, tray (800) may selectively couple with housing (304) in any other suitable fashion.

It should be understood that any of the above-described features and uses of trays (306, 606, 706, 800) may be interchanged among trays (306, 606, 706, 800) as desired. In other words, the above-described features are arbitrarily described in the context of a particular tray (306, 606, 706, 800), and not because such features are limited to such a particular tray (306, 606, 706, 800). Suitable ways in which the above-described features and uses of trays (306, 606, 706, 800) may be interchanged among trays (306, 606, 706, 800) will be apparent to those of ordinary skill in the art in view of the teachings herein.

It should also be understood that the configuration of walls (312) in housing (302) may provide fluid isolation among chambers (316). In other words, each chamber (316) may provide a discrete conduit for fluid communication between first lumen (117) and second lumen (119). Such fluid communication may thus be limited to only the chamber (316) that is oriented at the "12 o'clock position," with no fluid communication "bleeding into" any of the other chambers (316). Alternatively, tissue sample holder (302) may be configured such that chambers (316) are not completely fluidly isolated from each other; or such that chambers (316) are fluidly isolated in groups (e.g., set of three chambers (316) fluidly isolated from adjacent groups of three chambers (316), etc.).

It will be appreciated in view of the teachings herein that the removability of cup (303) and trays (306, 606, 706, 800) may permit a user to harvest a relatively large number of tissues samples in a relatively short period of time. Furthermore, the removability of cup (303) and trays (306, 606, 706, 800) may permit a user to remove unsatisfactory tissue samples from tissue sample holder (302) (e.g., using tweezers, etc.) and then re-engage trays (306, 606, 706, 800) and cup (303) for further sampling. Other suitable ways in which the removability and other properties of tissue sample holder (302) of the present example may be utilized will be apparent to those of ordinary skill in the art in view of the teachings herein. By way of example only, tissue sample holder (302) may be configured or used in accordance with any of the teachings of U.S. Pub. No. 2008/0214995, entitled "Presentation of Biopsy Sample by Biopsy Device," published Sep. 4, 2008, the disclosure of which is incorporated by reference herein.

It should also be understood that the tissue sample holders described herein may be used in a variety of types of biopsy devices, and do not necessarily need to be used in the particular biopsy devices described herein. For instance, the present application refers to and incorporates by reference various patents, published patent applications, and patent applications. The tissue sample holders described herein, as well as variations thereof, may be incorporated into any of the biopsy devices described in any of those patents, published patent applications, and patent applications.

IV. Exemplary Vacuum Control Module and Canister

As shown in FIG. 1, an exemplary vacuum canister (500) is configured to be coupled vacuum control module (400). Vacuum control module (400) is operable to induce a vacuum through vacuum canister (500), and such a vacuum may be communicated to biopsy probe (102). For instance, vacuum control module (400) may communicate a vacuum through tube (404), which may then communicate the vacuum through tissue sample holder (302) to cutter lumen (52) as described above. Vacuum control module (400) may also communicate a vacuum through tube (402) to a manifold of hub (60), which may then communicate the vacuum to vacuum lumen of outer cannula (12) as described above.

Furthermore, vacuum canister (500) is operable to collect fluids that are communicated from biopsy probe (102) during use of biopsy probe (102). Vacuum canister (500) may thus be regarded as providing a fluid interface between biopsy probe (102) and vacuum control module (400). Any suitable vacuum control module and vacuum canister may be used such as those described in U.S. Pub. 2008/0214955, entitled "Presentation of Biopsy Sample by Biopsy Device," published Sep. 4, 2008. Further, any other suitable component, system, technique, or device may be used with the suitable control module or vacuum canister.

As shown in FIG. 1, a tube (408) is fed into tube (402). Tube (410) is also fed into tube (402). In particular, a connector (446) connects saline tube (408) with tube (402). As shown, connector (446) is provided adjacent to canister (500), while connector (448) is provided near biopsy probe (102). In the present example, connectors (446) simply provide a constantly open conduit between tubes (410, 402) and tubes (408, 402), respectively. In other embodiments, connectors (446, 448) may have any other suitable components (e.g., valve, etc.). It will be appreciated in view of the disclosure herein that the configuration of tubes (402, 408, 410) and connectors (446, 448) permits any of a vacuum, vent, or saline to be communicated through tube (402). An exemplary determination of which of these will be communicated through tube (402) will be described in greater detail below. As also shown, saline bag (444) is coupled with tube (408) using any suitable conventional fitting.

Vacuum control module (400) of the present example also includes a motor (480) operable to control at least some components of holster (202). For instance, motor (480) may rotate drive cable (484), such as to actuate cutter (50) as described above. In particular, motor (480) may be part of a control module interface, such as one described in U.S. Non-Provisional patent application Ser. No. 12/337,814, entitled "CONTROL MODULE INTERFACE," filed on even date herewith, issued as U.S. Pat. No. 8,328,732 on Dec. 11, 2012, the disclosure of which is incorporated by reference herein. Biopsy device (100) may also include one or more encoders (not shown), which may be used to communicate data to such a control module interface relating to the position of cutter (50) and the position of housing (304) of tissue sample holder (302), etc. Such a control module interface may facilitate use of biopsy device (100) in an MRI environment, or in other settings. Of course, the features and functionality of vacuum control module (400) and vacuum canister (500) as described herein are mere examples.

V. Exemplary Modes of Operation

It will be appreciated in view of the disclosure herein that there are a variety of methods by which biopsy system (2) may be operated. For instance, regardless of the structures or techniques that are used to selectively control communication of fluid (e.g., saline, vacuum, venting, etc.), through tubes (402, 404, 408, 410) or otherwise within biopsy system (2), there are a variety of timing algorithms that may be used. Such timing algorithms may vary based on an operational mode selected by a user. Furthermore, there may be overlap among operational modes (e.g., biopsy system (2) may be in more than one operational mode at a given moment, etc.). In addition to fluid communication timing algorithms being varied based on a selected mode of operation, other operational aspects of biopsy system (2) may vary based on a selected operational mode. For instance, operation of tissue sample holder (302) may vary based on a selected operational mode, as may operation of cutter (50) and other components of biopsy system (2). Several merely exemplary operational modes exist, while others will be apparent to those of ordinary skill in the art in view of the teachings herein. Any suitable operational mode may be used include for example any suitable mode disclosed in U.S. Pub. 2008/0214955, entitled "Presentation of Biopsy Sample by Biopsy Device," published Sep. 4, 2008, the disclosure of which is incorporated herein by reference.

One example operation of biopsy system (2) will now be explained where needle portion (10) has been inserted into the breast of a patient. With needle portion (10) inserted, lateral and axial vacuum are applied. In particular, a vacuum is communicated through tubes (402, 404). Given the fluid connection of tube (402) with needle hub (60), as well as outer cannula (12), communication of a vacuum through tube (402) will draw a lateral vacuum relative to cannula lumen (20). Communication of a vacuum through tube (404) will draw an axial vacuum through cutter lumen (52), given the fluid connection of tube (404) to cutter lumen (52) via tissue sample holder (302) in this example.

With the axial and lateral vacuum applied as described above, cutter (50) is retracted axially. The axial retraction of cutter (50) will serve to "open" aperture (16), which results in tissue prolapsing into aperture (16) under the influence of the above-described vacuums. Cutter (50) may dwell in a retracted position for a certain period of time to ensure sufficient prolapse of tissue.

Next, cutter (50) is advanced distally to sever tissue that is prolapsed through aperture (16). As the distal end of cutter (50) passes the distal edge of aperture (16), such that cutter (50) "closes" aperture (16), the prolapsed tissue should be severed and at least initially contained within cutter lumen (52). Transverse openings should be configured such that at least one or more of transverse openings are not covered by cutter (50) when cutter (50) has reached a position to "close" aperture (16). With aperture (16) closed and a vent being provided by transverse openings through tube (402), an axial vacuum being communicated through cutter lumen (52) by tube (404) should draw the severed tissue sample proximally through cutter lumen (52) and into a tissue sample chamber (345) of tissue sample holder (302). Cutter (50) may be reciprocated one or more times through a slight range of motion at a distal position to sever any remaining portions that may have not been completely severed in the first pass of cutter (50).

Before tissue sample is communicated proximally through cutter lumen (52), with aperture (16) being closed by cutter (50), vacuum lumen (40) being vented by tubes (402, 410), and an axial vacuum being provided by tube (404) via cutter lumen (52), cutter (50) is retracted slightly to expose a portion of aperture (16) for a short period of time. During this time, saline may be provided at atmospheric pressure to vacuum lumen (40) by tubes (402, 408). Further retraction of cutter (50) exposes more transverse openings, thereby increasing fluid communication between vacuum lumen (40) and cannula lumen (20). Retraction of cutter (50) also exposes the pressure of the tissue cavity (from which tissue sample was obtained) to the distal surface of tissue sample. As a result of the slight retraction of cutter (50) in this particular example, the likelihood of atmospheric pressure being applied to the distal face of tissue sample may be increased to help ensure that severed tissue sample does not remain in needle portion (10) (a.k.a. a "dry tap"). Cutter (50) is then fully advanced distally, closing both aperture (16) and all transverse openings of outer cannula (12). Such "closure" of transverse openings may ensure that if medication is applied at this time (between samples) to reduce pain, it will reach the breast cavity through external openings in outer cannula (12) instead of being aspirated through transverse openings and through cutter lumen (52) and tissue sample holder (302).

With the cutter (50) being completely advanced (e.g., such that all transverse openings and aperture (16) are closed), and severed tissue sample being communicated proximally through cutter lumen (52) and into a chamber (316) by an axial vacuum drawn by tube (404), biopsy device (100) will be in a ready state. In this ready state, vacuum lumen (40) is vented to atmosphere, and axial vacuum tube (404) is sealed (a.k.a. "dead-headed").

It should be understood that tissue sample holder (302) may be easily incorporated into a variety of other biopsy devices. For instance, tissue sample holder (302) may be incorporated into a biopsy device constructed in accordance with any of the teachings of U.S. Non-Provisional patent application Ser. No. 12/337,874, entitled "MECHANICAL TISSUE SAMPLE HOLDER INDEXING DEVICE," filed on even date herewith, issued as U.S. Pat. No. 8,622,927 on Jan. 7, 2014, the disclosure of which is incorporated by reference herein; U.S. Non-Provisional patent application Ser. No. 12/337,720, entitled "BIOPSY DEVICE WITH SLIDING CUTTER COVER," filed on even date herewith, issued as U.S. Pat. No. 7,862,518 on Jan. 4, 2011, the disclosure of which is incorporated by reference herein; U.S. Non-Provisional patent application Ser. No. 12/337,942, entitled "TISSUE BIOPSY DEVICE WITH CENTRAL THUMBWHEEL," filed on even date herewith, published as U.S. Publication No. 2010/0160819 on Jun. 24, 2010, the disclosure of which is incorporated by reference herein. Alternatively, tissue sample holder (302) may be incorporated into any other type of biopsy device.

It should also be understood that biopsy device (100) may be coupled with a targeting set, such as any of the targeting sets disclosed in U.S. Non-Provisional patent application Ser. No. 12/337,986, entitled "MULTI-ORIENTATION TARGETING SET FOR MRI BIOPSY DEVICE," filed on even date herewith, published as U.S. Publication No. 2010/0160825 on Jun. 24, 2010, the disclosure of which is incorporated by reference herein; U.S. Pub. No. 2005/0277829, entitled "MRI BIOPSY APPARATUS INCORPORATING A SLEEVE AND A MULTI-FUNCTION OBTURATOR," published Dec. 15, 2005, the disclosure of which is incorporated by reference herein; U.S. Pub. No. 2007/0167736, entitled "MRI BIOPSY APPARATUS INCORPORATING AN IMAGEABLE PENETRATING PORTION," published Jul. 19, 2007, the disclosure of which is incorporated by reference herein; U.S. Pub. No. 2003/0199785, entitled "LOCALIZATION MECHANISM FOR AN MRI COMPATIBLE BIOPSY DEVICE," published Oct. 23, 2003, the disclosure of which is incorporated by reference herein; or U.S. Pub. No. 2007/0255170, entitled "BIOPSY CANNULA ADJUSTABLE DEPTH STOP," published Nov. 1, 2007, the disclosure of which is incorporated by reference herein. Still other suitable ways in which biopsy device (100) may be made and used will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A tissue sample holder configured to engage a biopsy probe and receive a tissue sample, the tissue sample holder comprising:
    (a) a housing including a plurality of chambers, wherein the chambers each extend along an axial direction, wherein each chamber is defined by an upper wall, a lower wall, and a pair of side walls, wherein the upper wall, lower wall, and side walls are unitary and form a continuous perimeter, wherein the housing further comprises:
        (i) an inner portion having a proximal edge and a distal edge, wherein the inner portion defines a central bore and further defines the lower walls of the chambers;
        (ii) an outer portion having a proximal edge and a distal edge, wherein the outer portion is coaxial with the inner portion and further defines the upper walls of the chambers; and
        (iii) a plurality of radially extending walls extending from the inner portion to the outer portion, wherein the radially extending walls define the side walls of the chambers; and
    (b) at least one tray, wherein the at least one tray is configured to be axially received within one or more of the plurality of chambers, wherein the at least one tray is configured to receive a tissue sample wherein the at least one tray comprises:
        (i) a pair of sidewalls, each sidewall having a proximal edge and a distal edge,
        (ii) a floor engaged with the sidewalls, the floor having a proximal edge and a distal edge, and
        (iii) a back wall coupled to the proximal edges of the sidewalls and the proximal edge of the floor.

2. The tissue sample holder of claim 1 wherein each chamber of the plurality of chambers comprises a proximal end and a distal end, wherein the proximal end is configured to receive a tray, wherein the distal end is configured to be positioned proximate to the probe, wherein the plurality of radially extending walls in the housing are positioned between the proximal end and the distal end.

3. The tissue sample holder of claim 2 wherein the distal end of each chamber of the plurality of chambers comprises an upper aperture and a lower aperture.

4. The tissue sample holder of claim 1, further comprising a tray retainer configured to engage the housing and to selectively engage the at least one tray, wherein the inner portion comprises at least one proximal receiving recess, wherein the at least one proximal receiving recess is positioned proximate to the central bore and the proximal edge of the inner portion, wherein the at least one proximal receiving recess is configured to engage the tray retainer.

5. The tissue sample holder of claim 4, wherein the tray retainer comprises:
    (i) a shaft having an exposed end and an unexposed end, and
    (ii) at least one locking member proximal the exposed end, wherein the tray retainer is configured to be received into the central bore by having the at least one locking member engage the at least one proximal receiving recess.

6. The tissue sample holder of claim 1, wherein the tray is configured to be received within a chamber of the plurality of chambers by first positioning the distal edges of the sidewalls of the tray into the respective chamber.

7. The tissue sample holder of claim 6, wherein the floor comprises a plurality of apertures.

8. The tissue sample holder of claim 1, further comprising a cup, wherein the cup is configured to be removably coupled with the biopsy probe, wherein the cup is further configured to cover the housing and the at least one tray.

9. A biopsy device, the biopsy device comprising:
    (a) a probe body;
    (b) a needle portion extending distally from the probe body, wherein the needle portion comprises a transverse tissue receiving aperture;
    (c) a hollow cutter positioned within the needle portion, wherein the cutter is translatable within the needle portion to sever a tissue sample from tissue protruding through the aperture, wherein the hollow cutter defines a cutter lumen; and
    (d) a tissue sample holder, wherein the tissue sample holder comprises:

(i) a housing, (ii) a plurality of chambers formed in the housing, wherein each of the chambers extends in an axial direction and is defined by a top surface of the housing, a bottom surface of the housing, and a pair of walls of the housing, wherein the axial direction is parallel with the cutter lumen, wherein the top surface, the bottom surface, and the walls of the housing are operable to rotate together unitarily, and (iii) a plurality of trays removably engaged with the chambers, wherein the trays are removable from the chambers in an axial direction, wherein each tray of the plurality of trays comprises a proximal wall configured to engage a proximal end of each of the chambers to substantially seal each of the chambers relative to each tray of the plurality of trays;

wherein the tissue sample holder is operable to selectively index a chamber of the plurality of chambers with the cutter lumen to receive a tissue sample in an indexed chamber.

10. The biopsy device of claim 9, wherein the tissue sample holder further comprises a tray retainer operable to selectively secure the trays within the tissue sample holder.

11. The biopsy device of claim 9, wherein the tissue sample holder further comprises an inner housing, wherein the inner housing defines the plurality of chambers, wherein the trays are removably engageable with the inner housing.

12. The biopsy device of claim 9, wherein each of the trays comprises a pair of sidewalls, a floor extending between each pair of sidewalls, wherein the proximal wall is integral with each pair of sidewalls and corresponding floor.

13. The biopsy device of claim 12, wherein the floor has a plurality of apertures formed therethrough.

14. The biopsy device of claim 9, wherein each tray defines a plurality of tissue sample chambers, wherein each tissue sample chamber of each tray is associated with a corresponding chamber of the plurality of chambers.

15. The biopsy device of claim 9, wherein the tissue sample holder is configured to redirect fluid communicated to the cutter lumen from a first direction to a second direction.

16. The biopsy device of claim 9, wherein the tissue sample holder is selectively engageable with the probe body, wherein the tissue sample holder comprises a release mechanism operable to selectively release the tissue sample holder relative to the probe body.

17. The biopsy device of claim 16, further comprising a tissue holder rotation shaft extending proximally from the probe body, wherein the release mechanism is configured to selectively engage the tissue holder rotation shaft.

18. A method of operating a biopsy device, wherein the biopsy device comprises:

(i) a needle having a tissue receiving aperture, the needle defining a needle axis, (ii) a cutter configured to sever tissue at the aperture, (iii) a lumen configured to communicate tissue severed by the cutter, and (iv) a tissue sample holder having at least one tray insertable into at least one chamber formed in a housing, wherein the at least one tray is defined by a pair of sidewalls, a floor engaged with the sidewalls, and a proximal wall coupled to a proximal edge of the sidewalls and the floor, wherein the at least one chamber is defined by a top surface of the housing, a bottom surface of the housing, and a pair of walls of the housing, and wherein the at least one tray is configured to receive tissue communicated through the lumen;

wherein the method comprises:

(a) inserting the at least one tray into the at least one chamber such that the proximal wall of the tray engages a proximal edge of the housing;

(b) capturing a tissue sample with the needle and the cutter;

(c) communicating the tissue sample through the lumen to a first chamber associated with the at least one tray;

(d) rotating the housing to index a second chamber relative to the lumen, wherein the act of rotating comprises simultaneously rotating the top surface of the housing, the bottom surface of the housing, and the walls of the housing, and (e) removing the at least one tray from the tissue sample holder by pulling the at least one tray in an axial direction parallel to the needle axis.

* * * * *